United States Patent
Adachi et al.

(10) Patent No.: US 9,479,880 B2
(45) Date of Patent: Oct. 25, 2016

(54) SPEECH-SOUND DISTINGUISHING ABILITY DETERMINATION APPARATUS, SPEECH-SOUND DISTINGUISHING ABILITY DETERMINATION SYSTEM, HEARING AID GAIN DETERMINATION APPARATUS, SPEECH-SOUND DISTINGUISHING ABILITY DETERMINATION METHOD, AND PROGRAM THEREOF

(71) Applicant: Panasonic Corporation, Osaka (JP)

(72) Inventors: Shinobu Adachi, Nara (JP); Yumiko Kato, Osaka (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 266 days.

(21) Appl. No.: 14/170,748

(22) Filed: Feb. 3, 2014

(65) Prior Publication Data
US 2014/0153729 A1 Jun. 5, 2014

Related U.S. Application Data

(63) Continuation of application No. PCT/JP2013/002649, filed on Apr. 19, 2013.

(30) Foreign Application Priority Data

Apr. 24, 2012 (JP) .................. 2012-098431

(51) Int. Cl.
| | | |
|---|---|---|
| H04R 25/00 | (2006.01) | |
| A61B 5/0484 | (2006.01) | |
| A61B 5/12 | (2006.01) | |

(52) U.S. Cl.
CPC ........... *H04R 25/70* (2013.01); *A61B 5/04845* (2013.01); *A61B 5/125* (2013.01); *H04R 2225/43* (2013.01)

(58) Field of Classification Search
CPC ..... H04R 25/70; H04R 25/30; H04R 25/552
USPC .......................................... 381/60, 314, 23.1
See application file for complete search history.

(56) References Cited

U.S. PATENT DOCUMENTS 6,067,467 A * 5/2000 John .................... A61B 5/0484
                                                        600/544
6,477,404 B1 * 11/2002 Yonce .................. A61B 5/7217
                                                        600/510

(Continued)

FOREIGN PATENT DOCUMENTS

| | | |
|---|---|---|
| CN | 102265335 A | 11/2011 |
| JP | 06-114038 A | 4/1994 |

(Continued)

OTHER PUBLICATIONS

International Search Report for corresponding International Application No. PCT/JP2013/002649 mailed Jul. 2, 2013.
Yoshitaka Yokoyama et al., "Distribution of Event-Related Potentials in Patients with Dementia", Therapeutic Research, vol. 14, No. 6, 1993, pp. 2485-2489.

(Continued)

*Primary Examiner* — Alexander Jamal
(74) *Attorney, Agent, or Firm* — Renner, Otto, Boisselle & Sklar, LLP

(57) ABSTRACT

In a speech discrimination ability determination system, an MMN determination section acquires, with respect to each of the first and second speech sounds, difference information between the event-related potential acquired during its output with the first occurrence frequency and the event-related potential acquired during its output with the second occurrence frequency, and determines whether a negative component exists in the difference information in predetermined time ranges after the first and second speech sounds are output. When the determination result indicates that the negative component exists, a discrimination ability determination section determines that the user discriminates the first and second speech sounds.

17 Claims, 16 Drawing Sheets

(56) References Cited

U.S. PATENT DOCUMENTS

| | | | |
|---|---|---|---|
| 2005/0018858 A1* | 1/2005 | John | A61B 5/121 381/60 |
| 2007/0191727 A1* | 8/2007 | Fadem | A61B 5/0002 600/544 |
| 2011/0188664 A1 | 8/2011 | Morikawa et al. | |
| 2012/0072213 A1 | 3/2012 | Adachi et al. | |
| 2012/0197153 A1* | 8/2012 | Kraus | A61B 5/743 600/545 |
| 2012/0239401 A1 | 9/2012 | Arakawa | |
| 2013/0274628 A1* | 10/2013 | Fausti | A61B 5/123 600/559 |

FOREIGN PATENT DOCUMENTS

| | | |
|---|---|---|
| JP | 09-038069 A | 12/1997 |
| JP | 2008-503261 A | 2/2008 |
| JP | 4838401 B | 10/2011 |
| JP | 2012-098643 A | 5/2012 |
| WO | WO 03/037186 A2 | 5/2003 |
| WO | WO 2006/009771 A1 | 1/2006 |
| WO | WO 2011/070972 A1 | 6/2011 |

OTHER PUBLICATIONS

Hideki Yoshida et al., "Evaluation of Synthesized Speeches and Noises by Using Mismatch Negativity", Biomedical Fuzzy Systems Association, vol. 11, No. 2, 2009, pp. 63-72.

Jishoukanrendeni (ERP) Manyuaru-P300 Wo Chushinni-(or "Event-Related Potential (ERP) Manual—mainly concerning P300-"), edited by Kimitaka Kaga et al., Shinohara Shuppan Shinsha, 1995, p. 30 and partial English translation.

Duncan et al., "Event-related potentials in clinical research: Guidelines for eliciting, recording, and quantifying mismatch negativity, P300, and N400", Clinical Neurophysiology 120 (2009) pp. 1883-1908.

Näätänen et al., "Mismatch Negativity—The Measure for Central Sound Representation Accuracy", Audiology & Neuro-Otology, 1997; 2, pp. 341-353.

Chinese Office Action and Search Report for corresponding Chinese Application No. 201380001420.5 dated Nov. 30, 2015 (including English translation of Search Report).

Davids et al., "The nature of auditory discrimination problems in children with specific language impairment: An MMN study", Neuropsychologia, 49, (2011), pp. 19-28.

* cited by examiner

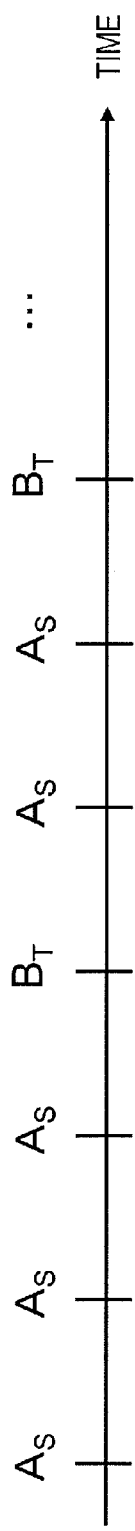
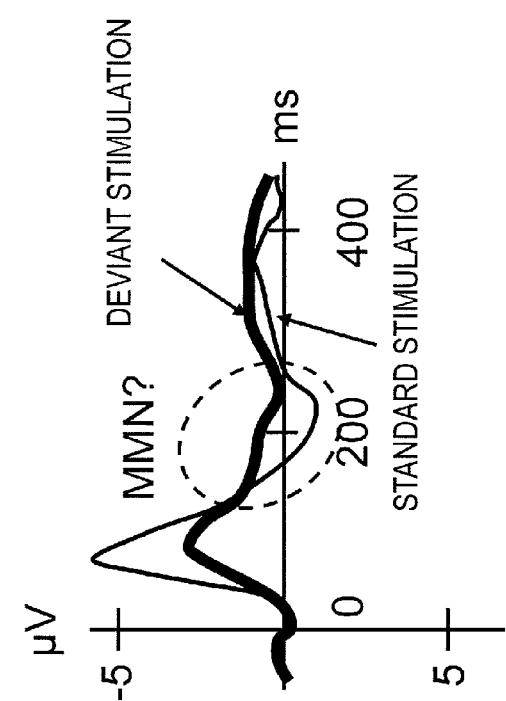
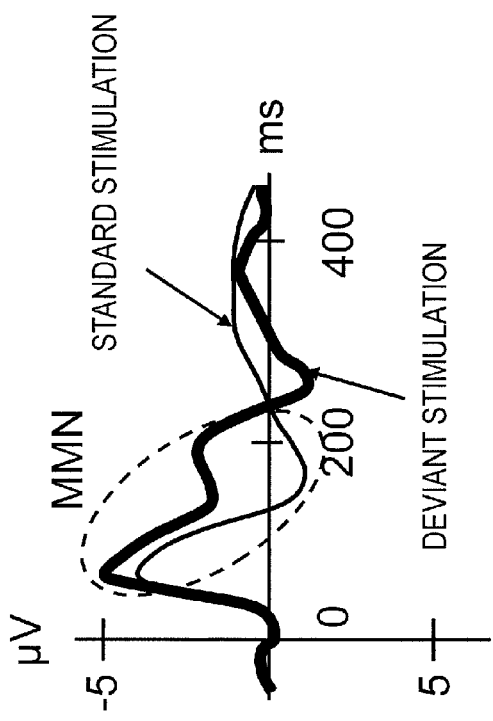
FIG.1A
FIG.1C
FIG.1B

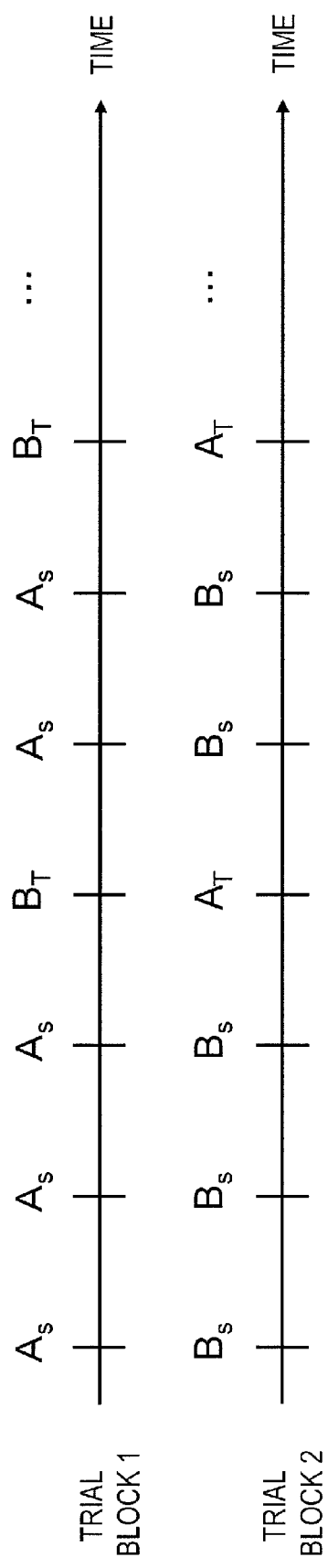
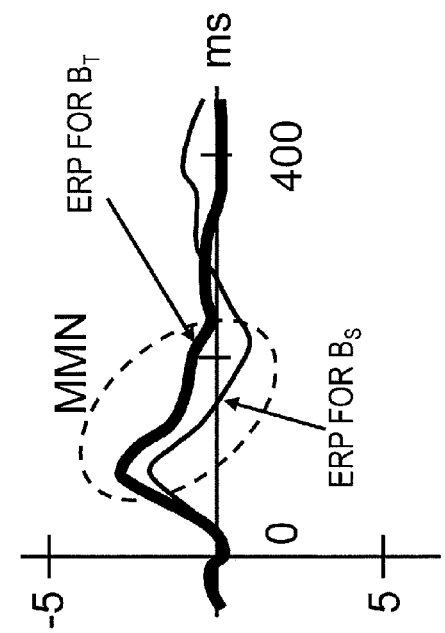
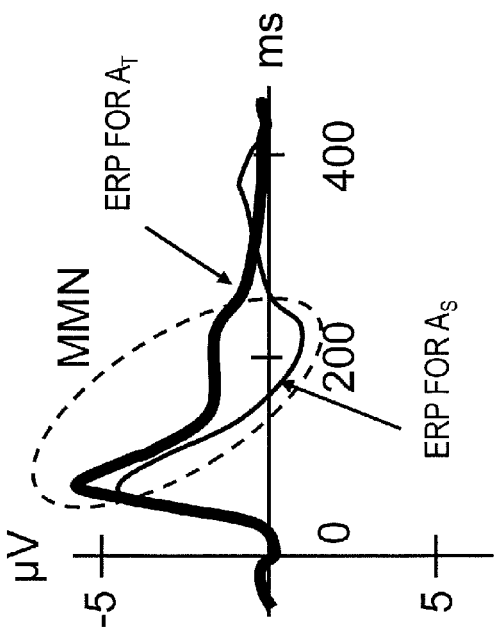
FIG.2A
FIG.2B
FIG.2C

FIG.3

| | MMN(B,A) | |
|---|---|---|
| | PRESENT | ABSENT |
| MMN(A,B) PRESENT | DISCRIMINATED | (POSSIBLY) NOT DISCRIMINATED |
| MMN(A,B) ABSENT | (POSSIBLY) NOT DISCRIMINATED | NOT DISCRIMINATED |

FIG. 4

| | MMN | |
|---|---|---|
| | PRESENT | ABSENT |
| N1 PRESENT (INDUCED RESPECTIVELY BY BOTH SOUND STIMULATIONS) | CORRECTLY DISCRIMINATED | HEARD BUT NOT DISCRIMINATED |
| INDUCED BY ONLY ONE SOUND STIMULATION | ONE OF THE CONSONANTS IS NOT HEARD | ELECTROENCEPHALOGRAM IS NOT BEING PROPERLY MEASURED |
| ABSENT (INDUCED BY NEITHER SOUND STIMULATION) | ELECTROENCEPHALOGRAM IS NOT BEING PROPERLY MEASURED | NEITHER CONSONANT IS HEARD |

FIG.9

| SPEECH SOUND | AUDIO FILE | CONSONANT LABEL |
|---|---|---|
| GA | ga.wav | g |
| DA | da.wav | d |

The 10-20 system

UPPER VIEW    FRONTAL VIEW

FIG.14

| SPEECH SOUND | AUDIO FILE | CONSONANT LABEL | FORMANT | | |
|---|---|---|---|---|---|
| | | | FIRST | SECOND | THIRD |
| GA | ga.wav | g | 500 Hz 60 dBSPL | 1500 Hz 55 dBSPL | 2500 Hz 60 dBSPL |
| DA | da.wav | d | 500 Hz 55 dBSPL | 1500 Hz 60 dBSPL | 3000 Hz 65 dBSPL |

SPEECH-SOUND DISTINGUISHING ABILITY DETERMINATION APPARATUS, SPEECH-SOUND DISTINGUISHING ABILITY DETERMINATION SYSTEM, HEARING AID GAIN DETERMINATION APPARATUS, SPEECH-SOUND DISTINGUISHING ABILITY DETERMINATION METHOD, AND PROGRAM THEREOF

This is a continuation of International Application No. PCT/JP2013/002649, with an international filing date of Apr. 19, 2013, which claims priority of Japanese Patent Application No. 2012-098431, filed on Apr. 24, 2012, the contents of which are hereby incorporated by reference.

BACKGROUND

1. Technical Field

The present application relates to a technique of speech discrimination ability determination. More specifically, the present application relates to a technique of improving speech-sound discrimination ability and a technique of determining a gain for a hearing aid, for use in hearing aid fitting and the like.

2. Description of the Related Art

Japanese National Phase PCT Laid-Open Publication No. 2008-503261 discloses that a mismatch negativity (MMN) component has come into wide use in developmental studies and sleep studies, as an evoked response testing system for neurological disorders. An "MMN component", which is a kind of event-related potential contained in an electroencephalogram signal, is a negative potential shift that is mainly induced in 100 ms to 250 ms from the presentation of an auditory stimulation. Since the paradigm for measuring an MMN component does not require the test subject to pay attention to a stimulation, this is suitable for the assessment of an infant or a sleeping user, for whom it is difficult to keep conscious attention.

Japanese Patent No. 4838401 discloses a speech sound intelligibility assessment system. The system described in Japanese Patent No. 4838401 determines the presence or absence of a positive component of event-related potential in a zone from 600 ms to 800 ms since a point in time of presenting a speech sound from an output section, and the presence or absence of a negative component of event-related potential in a zone from 100 ms to 300 ms since a point in time of presenting a speech sound. Based on the result of determining the presence or absence of a positive component and the result of determining the presence or absence of a negative component, an evaluation is made as to whether the user has clearly heard a presented speech sound or not.

SUMMARY

However, Japanese National Phase PCT Laid-Open Publication No. 2008-503261 and Japanese Patent No. 4838401 fail to disclose a method of determining speech discrimination ability utilizing an MMN component.

One non-limiting and exemplary embodiment of the present application provides a speech discrimination ability determination system for determining speech discrimination ability by using an MMN component.

In one general aspect, a speech discrimination ability determination system disclosed herein comprises: a biological signal measurement section for measuring an electroencephalogram signal of a user; a sound stimulation determination section for, by referring to a speech sound database storing information of a plurality of speech sounds, determining a first speech sound and a second speech sound which are different from each other; an output section for switching between: a first trial in which the first speech sound is output with a first occurrence frequency and the second speech sound is output with a second occurrence frequency different from the first occurrence frequency; and a second trial in which the first speech sound is output with the second occurrence frequency and the second speech sound is output with the first occurrence frequency; an event-related potential acquisition section for acquiring event-related potential contained in the electroencephalogram signal, the event-related potential acquisition section acquiring: an event-related potential based on a point of outputting the first speech sound being output with the first occurrence frequency as a starting point; an event-related potential based on a point of outputting the first speech sound being output with the second occurrence frequency as a starting point; an event-related potential based on a point of outputting the second speech sound being output with the first occurrence frequency as a starting point; and an event-related potential based on a point of outputting the second speech sound being output with the second occurrence frequency as a starting point; an MMN determination section for, with respect to each of the first speech sound and the second speech sound, acquiring difference information between the event-related potential acquired during its output with the first occurrence frequency and the event-related potential acquired during its output with the second occurrence frequency, and determining whether a negative component exists in the difference information in predetermined time ranges after the first speech sound and the second speech sound are output; and a discrimination ability determination section for, when a determination result by the MMN determination section indicates that the negative component exists, determining that the user discriminates the first speech sound and the second speech sound.

With a speech discrimination ability determination system according to one implementation of the present invention, it is possible to improve the precision of speech discrimination ability determination, by using an MMN component.

The general and specific implementation above can be realized by using a system, a method, or a computer program, or implemented by using a combination of a system, a method, and/or a computer program.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIGS. 1A to 1C are diagrams showing a conventional measurement paradigm for an MMN component and imaginary results thereof.

FIGS. 2A to 2C are diagrams showing a measurement paradigm for an MMN component which has been devised by the inventors and imaginary results thereof.

FIG. 3 is a diagram showing a determination criterion concerning speech discrimination ability based on the presence or absence of an MMN component.

FIG. 4 is a diagram showing a determination criterion concerning speech discrimination ability based on an N1 component and an MMN component.

FIG. 9 is a diagram showing an exemplary speech sound database (DB) according to Embodiment 1.

FIG. 14 is a diagram showing an exemplary speech sound DB according to Embodiment 2.

DESCRIPTION OF EMBODIMENTS

Figure 5:
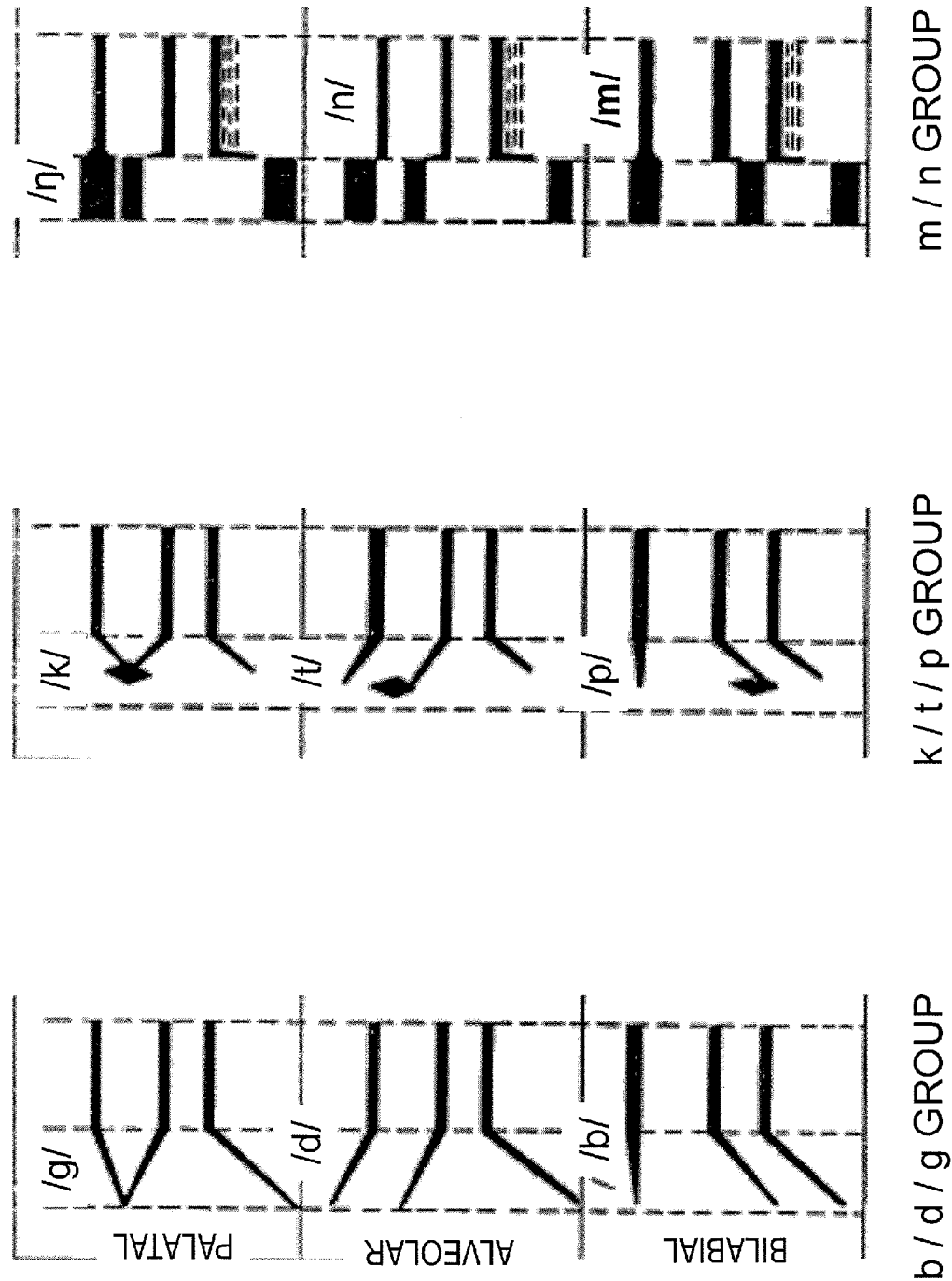
FIG. 5 is a diagram showing formant characteristics and changes in speech sound data in groups which are susceptible to confusion.

The definitions of the terms in the present specification will be described.

An "event-related potential (event-related potential: also referred to as "ERP")" is a fluctuation in the potential of an electroencephalogram (EEG) that occurs in response to a stimulation.

A "sound stimulation", also referred to as an auditory stimulation, is a sound which is presented to a user.

A "mismatch negativity (MMN) component" is a kind of event-related potential, and is a component concerning a negative potential shift of electroencephalogram which mainly occurs or is elicited in a time range from about 100 ms to 250 ms since a point in time of presenting a sound stimulation. As will be specifically described later, an MMN component is derived by, when plural kinds of sound stimulations are presented, through subtraction between the respective event-related potentials that have been induced by different kinds of sound stimulations.

An "N1 component" is a negative component of event-related potential which occurs in about 100 ms from a point in time of presenting a sound stimulation.

"Latency" is the time, based on the point of presenting a stimulation to serve as a starting point of event-related potential (e.g., an auditory stimulation or a visual stimulation) as a starting point, until a peak potential of a positive component or negative component of event-related potential occurs.

A "negative component" generally refers to a potential which is smaller than 0 μV. In a comparison between potentials, the potential having the greater negative value may be referred to as a negative component between the two.

A "positive component" generally refers to a potential which is greater than 0 μV. In a comparison between potentials, the potential having the greater value may be referred to as a positive component between the two.

In the present specification, in order to define a component of event-related potential, a point in time after the lapse of a predetermined time since a given point is expressed by referring to a "latency of about 100 ms", for example. This means possible inclusion of a range around the specific point of 100 ms in time. Generally speaking, there are 30 to 50 ms of differences (shifts) in event-related potential waveform between individuals, according to Table 1 on p. 30 of "JISHOUKANRENDENI (ERP) MANYUARU-P300 WO CHUSHINNI—(or "Event-Related Potential (ERP) Manual—mainly concerning P300-"), edited by Kimitaka KAGA et al., Shinohara Shuppan Shinsha, 1995)". Therefore, in the present specification, the terms "about Xms" and "near Xms" mean that a breadth of 30 to 50 ms may exist before or after Xms (e.g., 100 ms±30 ms, 200 ms±50 ms).

"Speech discrimination ability" means an ability to discriminate a speech sound.

An "occurrence frequency of a stimulation" means how often each kind of stimulation is presented among plural kinds of stimulations being presented. For example, when two types of stimulations a "standard stimulation" and a "deviant stimulation" (both will be described later) are to be presented, setting the standard stimulation to an occurrence frequency of 80% and the deviant stimulation to an occurrence frequency of 20% would mean that, when stimulations are presented a total of 10 times, the standard stimulation will have been presented 8 times, and the deviant stimulation will have been presented 2 times. In the present disclosure, there is no particular limitation as to the timing with which each kind of stimulation is presented. Given a population of 1, the standard stimulation may be set to an occurrence frequency of X (0<X<0.5) and the deviation may be set to an occurrence frequency of (1−X).

In the present disclosure, an ERP which is induced by a stimulation may be referred to as an "ERP corresponding to the stimulation".

A speech discrimination ability determination system according to each embodiment described below presents a speech sound to a user, analyzes the response (event-related potential) of an electroencephalogram which is induced by the speech sound stimulation, and determines a speech discrimination ability of the user. Prior to the description of the determination technique, the characteristics of an MMN component of event-related potential to be utilized as an index of speech discrimination ability will be generally described. Then, a speech discrimination ability determination method which has been devised by the inventors will be described in detail.

(Explanation of MMN Component)

An MMN component is a component of electroencephalogram that is induced when a user has discriminated a change in sound stimulation while plural kinds of sound stimulations which differ in frequency or sound pressure (corresponding to the "standard stimulation" and the "deviant stimulation" as defined in the present disclosure) are presented to the user in chronological order, for example. Generally speaking, in a situation where the standard stimulation is being presented a plurality of times, an MMN component is an amount of negative potential shift which is induced in a time range from 100 ms to 250 ms based on a rarely-presented deviant stimulation as a starting point.

An MMN component is considered to reflect, when a first stimulation and a second stimulation are consecutively presented, the course of a process of detecting a change, from a trace of perceptual memory that is created by the first stimulation, to the second stimulation.

A guideline has been proposed concerning a method of measuring an MMN component (Duncan et al., Event-related potentials in clinical research: Guideline for eliciting, recording, and quantifying mismatch negativity, P300, and N400, 2009).

An MMN component is derived by, when sound stimulations of different occurrence frequencies are presented, this being called an oddball paradigm, subtracting an electroencephalographic response that is caused by the standard stimulation being presented with a high occurrence frequency (e.g. 80%) from an electroencephalographic response that is caused by the deviant stimulation being presented with a low occurrence frequency (e.g. 20%). More specifically, in the present disclosure, it is derived as: MMN component=event-related potential which is induced by the deviant stimulation−event-related potential which is induced by the standard stimulation. Although pure tones are often used as the standard stimulation and the deviant stimulation, an MMN component will also be induced when sound stimulations other than pure tones are used.

The deviant stimulation may be any stimulation which differs to an extent that the participant can discriminate it over the standard stimulation. For example, any stimulation that differs from the standard stimulation in terms of frequency, duration, intensity, presence or absence of gaps, etc., can be regarded as a deviant stimulation. Note that "gaps" refer to the gaps between pulses in the case where one stimulation is composed of a plurality of pulses, rather than meaning the time interval between a plurality of stimulations.

Moreover, a deviant stimulation may be established when, in a situation where stimulations are being presented at periodic time intervals, a stimulation is not presented at the timing for presenting a stimulation. Since no actual stimulation is made, such a stimulation is referred to as a missing stimulation.

When measuring an MMN component, there is no need for an experimental participant to pay attention to the task during the measurement. Therefore, use of an MMN component will be effective for evaluating the response of a person who cannot maintain attention for a long time (i.e., an infant or a patient).

There are reports on the MMN component in the case where speech sounds are used as sound stimulations. For example, to Finnish speakers, Naatanen et. al presented a standard stimulation of /e/, and a deviant stimulation of /O~/ (where "~" is actually over the "O"; the same will always apply below), which is only found in the Estonian language, or /O••/ (where "••" is actually over the "O"; the same will always apply below), which is found in the Finnish language. In this case, although the physical difference between the standard stimulation and the deviant stimulation was greater with /O~/ than with /O••/, a greater MMN component existed for /O••/ (Näätänen et al., Mismatch Negativity—The Measure for Central Sound Representation Accuracy, 1997). This indicates a possibility that an MMN component can be used as a tool for examining a cerebral process on language or a learning process.

In the conventional studies on the MMN component, based on the premise that sound stimulations were audible to the participant, differences in the central process for sound information which was input to the sensory system (e.g. a difference between the mother language and another language) were examined.

However, by using the conventional studies, it is difficult to determine the discrimination ability of sound stimulations with respect to a person suffering from hypacusia because a person suffering from hypacusia may not hear, or have a difficulty in hearing, a sound stimulation depending on conditions, e.g., the frequency band.

As mentioned above, an MMN component is also induced by a missing stimulation. Therefore, if any of the sound stimulations that were presented in order to examine discrimination ability was not heard, the event that it was not heard serves as a missing stimulation to induce an MMN component.

Therefore, with respect to a person suffering from hypacusia, it is impossible to make any distinction between an MMN component which is induced because of a discrimination between the two kinds of sound stimulations being correctly made and an MMN component which is induced because of one of the sound stimulations not being heard. This leads to a possibility that, even if a sound stimulation is not heard, the wrong determination may be made that there exists discrimination ability.

This is a problem which does not manifest itself until attempting to determine a speech-sound discrimination ability by using speech sounds, of which frequency and intensity are difficult to control, as sound stimulations.

There is another problem in determining speech discrimination ability based on an MMN component as an index, when different speech sounds are used as the standard stimulation and the deviant stimulation.

That is, it becomes more difficult to determine the presence or absence of an MMN component. A large difference exists between the physical characteristics of a standard stimulation and the physical characteristics of a deviant stimulation. As used herein, the physical characteristics may be changes over time in frequency construction and intensity, for example. These differences exert a great influence (difference) on the ERP that is induced by each stimulation. It is difficult to identify whether a difference in event-related potential has been induced purely by the deviant stimulation, or by the physical characteristics of the speech sound. That is, determination of the presence or absence of an MMN component is also made difficult. This results in a possibility that the result of discrimination ability determination may be more erroneous. In an audio, changes over time in its frequency construction and intensity constitute its own information; therefore, audios that have been modified to equalize these may make it difficult to determine speech discrimination ability.

(Findings of the Inventors)

In view of the above two problems, the inventors have devised a novel method of determining speech discrimination ability which reduces misdeterminations due to the influence of sound stimulations not being heard and the influence of greatly differing physical characteristics of sound stimulations.

First, in order to solve the problem of misdetermination of discrimination ability due to sound stimulations not being heard, the inventors have devised a method which involves conducting a hearing determination using an N1 component of ERP prior to a discrimination determination based on an MMN component.

Next, in order to solve the problem of misdetermination due to differences in physical characteristics between a plurality of speech sound stimulations, the inventors have defined a trial block in which a speech sound is used as the standard stimulation and a trial block in which the same speech sound is used as the deviant stimulation. Then, they have devised a method of subtracting an ERP corresponding to the standard stimulation from an ERP corresponding to the deviant stimulation, and determining the presence or absence of an MMN component using this subtraction waveform.

By utilizing these methods, a technique of determining speech discrimination ability of a person suffering from hypacusia by using ERP is realized for the first time. The inventors have also found that a relatively high determination precision can be maintained. These will be described in detail below. For convenience of explanation, the latter method will be described first.

FIGS. 1A to 1C show two kinds of stimulations that are presented for MMN measurement, and imaginary ERP waveforms to be induced by such stimulations.

FIG. 1A shows standard stimulations ($A_S$) and deviant stimulations ($B_T$) in an MMN component measurement. In the present application, different kinds of sound stimulations are distinguished by letters A and B, and the standard stimulation and the deviant stimulation are distinguished by subscripts S and T.

FIG. 1A shows an example where the standard stimulation ($A_S$) is presented with a high occurrence frequency while the deviant stimulation ($B_T$) is presented with a low occurrence frequency. An MMN component is induced when the standard stimulation is presented with a high occurrence frequency and the deviant stimulation is presented with a low occurrence frequency. Usually, an MMN can be determined from eq. 1 below.

$$\text{MMN}=(\text{ERP induced by } B_T)-(\text{ERP induced by } A_S) \quad \text{(eq. 1)}$$

As expressed by eq. 1, the MMN component is obtained by subtracting an ERP corresponding to the standard stimulation from an ERP corresponding to the deviant stimulation. FIG. 1B shows an imaginary ERP waveform in the case where there is little difference between the physical characteristics of the standard stimulation and the physical characteristics of the deviant stimulation, whereas FIG. 1C shows an imaginary ERP waveform in the case where the difference is large. Each shows a time waveform whose starting point is defined by the point of presenting each stimulation.

As indicated by the above guideline, when there is little difference in physical characteristics between the standard stimulation and the deviant stimulation (FIG. 1B), there is hardly any influence of the physical characteristics of the sound stimulations, and thus it is easy to determine the presence or absence of an MMN component.

Now, the standard stimulation and the deviant stimulation having little difference in physical characteristics means, for example, their frequencies being within 10% of each other (e.g., a standard stimulation of 1000 Hz and a deviant stimulation of 1100 Hz) or their sound pressures being within 10% of each other (e.g., a standard stimulation of 60 dBSPL and a deviant stimulation of 66 dBSPL). Whenever the difference between the standard stimulation and the deviant stimulation cannot be considered little, it is to be considered as falling into the case of greatly differing physical characteristics, which will be described next.

When the physical characteristics of frequency and intensity greatly differ, as is the case with speech sounds (FIG. 1C), it is difficult to determine the presence or absence of an MMN component. It is considered that use of speech sounds as sound stimulations will often result into the case of FIG. 1C.

It must be noted here that the electroencephalographic response of a test subject would differ depending on the physical characteristics of each of sound stimulations A and B. This makes it difficult, when the electroencephalogram that is induced by the standard stimulation $A_S$ differs from the electroencephalogram that is induced by the deviant stimulation $B_T$, to distinguish whether it is a difference in electroencephalographic response that is associated with deviation or a difference that is associated with the physical characteristics of the sound stimulations.

Therefore, the inventors have devised a method where an ERP is measured in both a trial block in which a certain speech sound is presented as the standard stimulation and a trial block in which the same speech sound is presented as the deviant stimulation, such that a difference between the same sound stimulation being the deviant stimulation or the standard stimulation is defined as an MMN component.

FIG. 2A shows an MMN component measurement paradigm which has been devised by the inventors, and imaginary results thereof.

In FIG. 2B, the ERP caused by $A_S$ in Trial block 1 and the ERP corresponding to $A_T$ in Trial block 2 are compared, thus measuring a discrimination ability between sound stimulation A and sound stimulation B. Sound stimulation $A_S$ and sound stimulation $A_T$ are identical in physical characteristics.

An electroencephalogram caused by sound stimulation A is measured in Trial block 1, which is an environment where sound stimulation A steadily occurs, and an electroencephalogram is measured when sound stimulation A occurs in Trial block 2, which is an environment where sound stimulation B steadily occurs; and a difference MMN(A, B) therebetween is measured as indicated by eq. 2.

$$\text{MMN}(A,B)=(\text{ERP caused by } A_T)-(\text{ERP caused by } A_S) \quad \text{(eq. 2)}$$

If the test subject is able to recognize that sound stimulation A is distinct from sound stimulation B in the sound stimulation B environment, then the value of MMN(A, B) will be more negative than a predetermined value.

Similarly, in FIG. 2C, in order to measure a discrimination ability for sound stimulation B, MMN(B, A) is measured as indicated by eq. 3.

$$\text{MMN}(B,A)=(\text{ERP caused by } B_T)-(\text{ERP caused by } B_S) \quad \text{(eq. 3)}$$

Then, as indicated by eq. 4, Sum, which is a sum of MMN(A,B) and MMN(B,A), is determined. Sum is a mathematical expression used in MMN determination.

$$\text{Sum}=\text{MMN}(A,B)+\text{MMN}(B,A) \quad \text{(eq. 4)}$$

The result from eq. 4 is subjected to threshold processing to determine the presence or absence of an MMN. If it is greater than a predetermined threshold value (criterion), it is determined that an MMN component is absent, and if it is equal to or less than the predetermined threshold value (criterion), it is determined that an MMN component is present.

By doing so, it becomes possible to determine the presence or absence of an MMN component away from the influence that different physical characteristics of sound stimulations would exert on an evoked response, whereby misdetermination is reduced.

For example, the presence or absence of an MMN component is determined depending on whether a negative component around a latency of about 200 ms, in a subtraction waveform obtained by subtracting an ERP caused by the standard stimulation from an ERP caused by the deviant stimulation, is smaller than a predetermined criterion or not. Specifically, if the potential of the negative component around a latency of about 200 ms is greater than the predetermined criterion, it is determined that an MMN component is absent; if it is equal to or less than the predetermined criterion, it is determined that an MMN component is present.

In the case of using the amplitude of a negative component (i.e., the absolute value of a negative component) to determine the presence or absence of an MMN component, the presence or absence of an MMN component may be determined based on whether the absolute value of the negative component is greater than a predetermined criterion or not. For example, if the amplitude of the negative component is equal to or greater than the predetermined criterion, it may be determined that an MMN component is present; if the amplitude of the negative component is smaller than the predetermined criterion, it may be determined that an MMN component is absent. Alternatively, the amplitude of the waveforms of the standard stimulation and the deviant stimulation or the subtraction waveform around a latency of about 200 ms may be subjected to linear discrimination.

Figure 16:
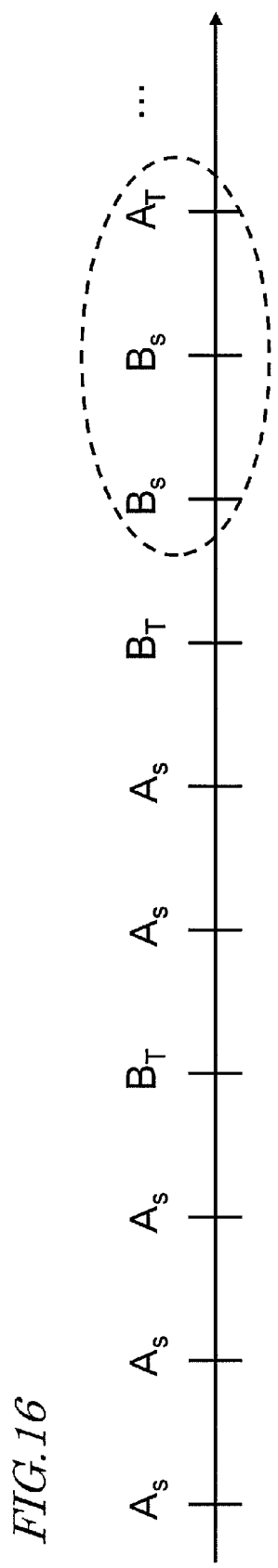
FIG. 16 is a diagram showing another method of outputting sound stimulations.

As for the waveform of the ERP corresponding to sound stimulation $A_S$ in Trial block 1, it is desirable to use a waveform which is as immune to $B_T$ stimulation as possible. Specifically, a steady electroencephalogram measurement with respect to $A_T$ would be enabled by avoiding the use of the response caused by any $A_S$ that immediately follows the presentation of $B_T$ sound stimulation. As shown in FIG. 16, rather than effecting separation into Trial block 1 and Trial block 2, sound stimulation A and sound stimulation B may be presented in random order, such that when one of the stimulation keeps occurring a plurality of times, the second and subsequent stimulations are regarded as standard stimulations, and that, after the one stimulation has kept occurring a plurality of times, if the other stimulation is presented, this is regarded as a deviant stimulation.

FIG. 3 shows a method of determining speech discrimination ability based on the presence or absence of an MMN component in the paradigm which has been conceived by the inventors. FIG. 3 shows determination results when two kinds of sound stimulations are used for instance. The determination results respectively indicating presence and absence of an MMN component for each of speech sound A and speech sound B produce the four statuses shown in FIG. 3. For example, if an MMN component is induced for both of speech sound A and speech sound B, it is determined that the user discriminates the speech sounds.

On the other hand, if an MMN component is induced for neither speech sound A nor speech sound B, it is determined that the user does not discriminate the speech sounds. Furthermore, if an MMN component is induced for only one of them, it is determined that there may possibly be no discrimination ability; or more simply, it may be determined that there is no discrimination ability. In this case, in order to realize a more precise determination of discrimination ability, electroencephalogram measurement may be continued and stimulation may be repeated until an identical result as to the presence or absence of an MMN component is reached for both sound stimulations.

Next, a method of reducing misdetermination due to the sound stimulations not being heard by the user will be described. The inventors have arrived at the concept of providing a step of determining whether a sound stimulation is heard by the user with the use of an N1 component of ERP corresponding to the sound stimulation. Since an N1 component is induced as a reflection of an auditory input reaching the cerebral cortex, a determination as to being heard or not heard can be made based on the N1 component as an index.

In order to realize a highly precise determination free from the influence of noises that mix into the electroencephalogram, the ERP to be used for determining the presence or absence of an N1 component may be obtained by taking an arithmetic mean for each kind of stimulation, irrespective of standard stimulation or deviant stimulation. Moreover, in order to account for the influence of habituation of electroencephalogram due to repetition of standard stimulations, an ERP corresponding to the current sound stimulation may be subjected to arithmetic mean only when the current sound stimulation differs from the immediately previous sound stimulation, and the presence or absence of an N1 component may be determined from such ERP.

FIG. 4 shows a method of speech discrimination ability determination that has been devised by the inventors, which is based on the presence or absence of an N1 component and the presence or absence of an MMN component. For simplicity of explanation, the presence or absence of an MMN component will be determined as follows: it is present if an MMN component is induced for both sound stimulations in FIG. 3; otherwise, it is absent. When an N1 component has been induced to every speech sound that has been presented as a sound stimulation, based on the presence or absence of an MMN component, a "correctly discriminated" determination is made if an MMN component is present, and a "heard but not discriminated" determination is made if an MMN component is absent.

If an N1 component has not been induced for either sound stimulation but an MMN component is present, then it is determined that one of the consonant is not heard. If an N1 component is induced for none of the sound stimulations and an MMN component is absent, it is determined that none of the consonants is heard. If an N1 component is not induced for any consonant and an MMN component is absent, and also if an N1 component is induced for none of the sound stimulations but an MMN component is present, it is determined that the electroencephalogram is not being properly measured. In this case, electroencephalogram measurement may be repeated until any other determination result is obtained.

Hereinafter, a method of hearing aid gain adjustment based on results of speech discrimination ability determination will be described. Note that "gain" means an amount by which a sound is amplified (amount of gain).

From conventional studies concerning audio, it is known that the transient characteristics of formants when a transition occurs from a consonant to a subsequent vowel serve a large role in speech sound discrimination.

Therefore, in the present specification, sounds including consonants as well as a transient state from any consonant to any vowel are used as sound stimulations for speech discrimination ability determination. However, this is an example. Each sound stimulation may be an entire speech sound including a vowel, or each sound stimulation may be a sound in a predetermined time range from the rise of a consonant.

The inventors have considered that it is possible to improve the speech discrimination ability through a gain adjustment of the frequencies of formants of a sound stimulation including a transient state from a consonant to a vowel. Formant are peaks in an audio spectrum, denoted as first, second, and so on in ascending order of frequency. The formant frequency relates to the vocal tract shape, and individual differences and gender differences also contribute to formant differences.

FIG. 5 shows formants of voiced plosive/affricative/fricative (b/d/g group), nasals (m/n group), and unvoiced consonants (k/t/p group), which are difficult to hear for a person with sensorineural hearing loss and likely to cause confusions (Kazuo NAKATA, audio, 1977, P165). In FIG. 5, the vertical axis represents frequency, and the horizontal axis represents time. In FIG. 5, solid lines indicate formants of each speech sound.

In each graph of FIG. 5, a broken line at the left end represents the start time of a consonant; the middle broken line represents the start time of a vowel; and the span from the broken line at the left end to the middle broken line represents a transient state from the consonant to the vowel. As shown in FIG. 5, among the speech sounds within each group, the formants have different transient characteristics. In particular, the transient characteristics of the second and third formants significantly differ in the b/d/g group and in the m/n group, whereas the frequency of the second formant significantly differs in the m/n group.

For example, assume that, when /g/ and /d/ are used as sound stimulations, an N1 component was induced for both, but no MMN component was induced. In this case, the gain is to be enhanced at the frequencies of the second and third formants, which exhibit significant differences between /g/ and /d/. The frequency of the second or third formant to be subjected to gain adjustment may be the center frequency of the frequency band of the transient state, or the first frequency of the transient state, for example. Alternatively, it may be the frequency of any formant in a predetermined time from the beginning of the consonant, or the frequency band across the entire transient state may be subjected to gain adjustment. Alternatively, when an N1 component was induced for neither, for example, an adjustment may be made to increase the overall gain, irrespective of the formant frequencies of the sound stimulation.

According to the above findings of the inventors, one implementation of the present invention for realizing speech discrimination ability determination is as follows, in outline.

A speech discrimination ability determination system as one implementation of the present invention comprises: a biological signal measurement section for measuring an electroencephalogram signal of a user; a sound stimulation determination section for, by referring to a speech sound database storing information of a plurality of speech sounds, determining a first speech sound and a second speech sound which are different from each other; an output section for switching between: a first trial in which the first speech sound is output with a first occurrence frequency and the second speech sound is output with a second occurrence frequency different from the first occurrence frequency; and a second trial in which the first speech sound is output with the second occurrence frequency and the second speech sound is output with the first occurrence frequency; an event-related potential acquisition section for acquiring event-related potential contained in the electroencephalogram signal, the event-related potential acquisition section acquiring: an event-related potential based on a point of outputting the first speech sound being output with the first occurrence frequency as a starting point; an event-related potential based on a point of outputting the first speech sound being output with the second occurrence frequency as a starting point; an event-related potential based on a point of outputting the second speech sound being output with the first occurrence frequency as a starting point; and an event-related potential based on a point of outputting the second speech sound being output with the second occurrence frequency as a starting point; an MMN determination section for, with respect to each of the first speech sound and the second speech sound, acquiring difference information between the event-related potential acquired during its output with the first occurrence frequency and the event-related potential acquired during its output with the second occurrence frequency, and determining whether a negative component exists in the difference information in predetermined time ranges after the first speech sound and the second speech sound are output; and a discrimination ability determination section for, when a determination result by the MMN determination section indicates that the negative component exists, determining that the user discriminates the first speech sound and the second speech sound.

In one embodiment, for example, the output section outputs the first speech sound and the second speech sound with the first occurrence frequency being X (0<X<0.5) and the second occurrence frequency being (1−X).

In one embodiment, for example, the MMN determination section determines that the negative component exists when determining that an event-related potential which is equal to or less than a predetermined threshold value exists in the difference information in the predetermined time ranges after the first speech sound and the second speech sound are output, and that the negative component does not exist when determining that an event-related potential which is greater than the predetermined threshold value exists.

In one embodiment, for example, the predetermined time range is a time range from 100 ms to 250 ms.

In one embodiment, the system further comprises an N1 determination section for determining whether an N1 component exists in a time range from 50 ms to 150 ms based on a point in time of outputting each of the first speech sound and the second speech sound as a starting point, the N1 component being a negative component of event-related potential, wherein, when a determination result by the N1 determination section indicates that the N1 component exists and the determination result by the MMN determination section indicates that the negative component exists, the discrimination ability determination section determines that the user discriminates the first speech sound and the second speech sound.

In one embodiment, for example, the N1 determination section determines that the N1 component exists when determining that an event-related potential which is equal to or less than a predetermined threshold value exists in predetermined time ranges after the first speech sound and the second speech sound are output, and that the N1 component does not exist when determining that an event-related potential which is greater than the predetermined threshold value exists.

In one embodiment, for example, when the determination result by the N1 determination section indicates that the N1 component exists and the determination result by the MMN determination section indicates that the negative component does not exist, the discrimination ability determination section determines that the user hears the first speech sound and the second speech sound but does not discriminate between the first speech sound and the second speech sound.

In one embodiment, the system further comprises an N1 determination section for determining whether an N1 component exists in a time range from 50 ms to 150 ms based on a point in time of outputting each of the first speech sound and the second speech sound as a starting point, the N1 component being a negative component of event-related potential, wherein, when a determination result by the N1 determination section indicates that the N1 component does not exist for either one of the first speech sound and the second speech sound and the determination result by the MMN determination section indicates that the negative component exists, the discrimination ability determination section determines that the user does not discriminate either one of the first speech sound and the second speech sound.

In one embodiment, the system further comprises an N1 determination section for determining whether an N1 component exists in a time range from 50 ms to 150 ms based on a point in time of outputting each of the first speech sound and the second speech sound as a starting point, the N1 component being a negative component of event-related potential, wherein, when the determination result by the N1 determination section indicates that the N1 component exists for either one of the first speech sound and the second speech sound and the determination result by the MMN determination section indicates that the negative component does not exist, the discrimination ability determination section determines that the biological signal measurement section is not properly measuring the electroencephalogram signal.

In one embodiment, the system further comprises an N1 determination section for determining whether an N1 component exists in a time range from 50 ms to 150 ms based on a point in time of outputting each of the first speech sound and the second speech sound as a starting point, the N1 component being a negative component of event-related potential, wherein, when the determination result by the N1 determination section indicates that the N1 component exists for neither the first speech sound nor the second speech sound and the determination result by the MMN determination section indicates that the negative component exists, the discrimination ability determination section determines that the biological signal measurement section is not properly measuring the electroencephalogram signal.

In one embodiment, the system further comprises a gain determination section for deciding an increase in a gain concerning a frequency at which a large formant frequency differences exists between the first speech sound and the second speech sound when the determination result by the discrimination ability determination section indicates that the user does discriminates neither the first speech sound nor the second speech sound.

In one embodiment, the system comprises a gain determination section for deciding an increase in gain across all audible frequencies when the determination result by the discrimination ability determination section indicates that the user hears neither the first speech sound nor the second speech sound.

In one embodiment, for example, the output section performs the first trial, and after the number of times of outputting the first speech sound has reached a predetermined number of times, switches from the first trial to the second trial.

A speech discrimination ability determination apparatus as another implementation of the present invention is a speech discrimination ability determination apparatus for use in a speech discrimination ability determination system that switches between: a first trial in which a first speech sound is output with a first occurrence frequency and the second speech sound is output with a second occurrence frequency different from the first occurrence frequency; and a second trial in which the first speech sound is output with the second occurrence frequency and the second speech sound is output with the first occurrence frequency, comprising: an event-related potential acquisition section for acquiring event-related potential contained in an electroencephalogram signal measured by a biological signal measurement section, the event-related potential acquisition section acquiring: an event-related potential based on a point of outputting the first speech sound being output with the first occurrence frequency as a starting point; an event-related potential based on a point of outputting the first speech sound being output with the second occurrence frequency as a starting point; an event-related potential based on a point of outputting the second speech sound being output with the first occurrence frequency as a starting point; and an event-related potential based on a point of outputting the second speech sound being output with the second occurrence frequency as a starting point; an MMN determination section for, with respect to each of the first speech sound and the second speech sound, acquiring difference information between the event-related potential acquired during its output with the first occurrence frequency and the event-related potential acquired during its output with the second occurrence frequency, and determining whether a negative component exists in the difference information in predetermined time ranges after the first speech sound and the second speech sound are output; and a discrimination ability determination section for, when a determination result by the MMN determination section indicates that the negative component exists, determining that the user discriminates the first speech sound and the second speech sound.

A hearing aid gain determination apparatus as still another implementation of the present invention is a hearing aid gain determination apparatus for use in a speech discrimination ability determination system that switches between: a first trial in which a first speech sound is output with a first occurrence frequency and the second speech sound is output with a second occurrence frequency different from the first occurrence frequency; and a second trial in which the first speech sound is output with the second occurrence frequency and the second speech sound is output with the first occurrence frequency, comprising: an event-related potential acquisition section for acquiring event-related potential contained in an electroencephalogram signal measured by a biological signal measurement section, the event-related potential acquisition section acquiring: an event-related potential based on a point of outputting the first speech sound being output with the first occurrence frequency as a starting point; an event-related potential based on a point of outputting the first speech sound being output with the second occurrence frequency as a starting point; an event-related potential based on a point of outputting the second speech sound being output with the first occurrence frequency as a starting point; and an event-related potential based on a point of outputting the second speech sound being output with the second occurrence frequency as a starting point; an MMN determination section for, with respect to each of the first speech sound and the second speech sound, acquiring difference information between the event-related potential acquired during its output with the first occurrence frequency and the event-related potential acquired during its output with the second occurrence frequency, and determining whether a negative component exists in the difference information in predetermined time ranges after the first speech sound and the second speech sound are output; a discrimination ability determination section for, when a determination result by the MMN determination section indicates that the negative component exists, determining that the user discriminates the first speech sound and the second speech sound; and a gain determination section for, by referring to a predetermined determination criterion, determining a gain for a hearing aid based on the difference information.

A speech discrimination ability determination method as still another implementation of the present invention comprises the steps of: by referring to a speech sound database storing information of a plurality of speech sounds, determining a first speech sound and a second speech sound which are different from each other; measuring an electroencephalogram signal of a user; performing a first trial in which the first speech sound is output with a first occurrence frequency and the second speech sound is output with a second occurrence frequency different from the first occurrence frequency; performing a second trial in which the first speech sound is output with the second occurrence frequency and the second speech sound is output with the first occurrence frequency; acquiring event-related potential contained in the electroencephalogram signal, the step acquiring: an event-related potential based on a point of outputting the first speech sound being output with the first occurrence frequency as a starting point; an event-related potential based on a point of outputting the first speech sound being output with the second occurrence frequency as a starting point; an event-related potential based on a point of outputting the second speech sound being output with the first occurrence frequency as a starting point; and an event-related potential based on a point of outputting the second speech sound being output with the second occurrence frequency as a starting point; with respect to each of the first speech sound and the second speech sound, acquiring difference information between the event-related potential acquired during its output with the first occurrence frequency and the event-related potential acquired during its output with the second occurrence frequency, and determining whether a negative component exists in the difference information in predetermined time ranges after the first speech sound and the second speech sound are output; and when a determination result by the determining step indicates that the negative component exists, determining that the user discriminates the first speech sound and the second speech sound.

A computer program as still another implementation of the present invention is a computer program to be executed by a computer mounted in a speech discrimination ability determination apparatus of a speech discrimination ability determination system, wherein the computer program causes the computer to execute the steps of: receiving an electroencephalogram signal of a user measured by a biological signal measurement section; by referring to a speech sound database storing information of a plurality of speech sounds, determining a first speech sound and a second speech sound which are different from each other; performing a first trial in which the first speech sound is output with a first occurrence frequency and the second speech sound is output with a second occurrence frequency different from the first occurrence frequency; performing a second trial in which the first speech sound is output with the second occurrence frequency and the second speech sound is output with the first occurrence frequency; acquiring event-related potential contained in the electroencephalogram signal, the step acquiring: an event-related potential based on a point of outputting the first speech sound being output with the first occurrence frequency as a starting point; an event-related potential based on a point of outputting the first speech sound being output with the second occurrence frequency as a starting point; an event-related potential based on a point of outputting the second speech sound being output with the first occurrence frequency as a starting point; and an event-related potential based on a point of outputting the second speech sound being output with the second occurrence frequency as a starting point; with respect to each of the first speech sound and the second speech sound, acquiring difference information between the event-related potential acquired during its output with the first occurrence frequency and the event-related potential acquired during its output with the second occurrence frequency, and determining whether a negative component exists in the difference information in predetermined time ranges after the first speech sound and the second speech sound are output; and when a determination result by the MMN determination section indicates that the negative component exists, determining that the user discriminates the first speech sound and the second speech sound.

Embodiment 1

Hereinafter, first, the speech discrimination ability determination system will be described in outline. Then, the construction and operation of a speech discrimination ability determination system including a speech discrimination ability determination apparatus will be described.

Figure 6:
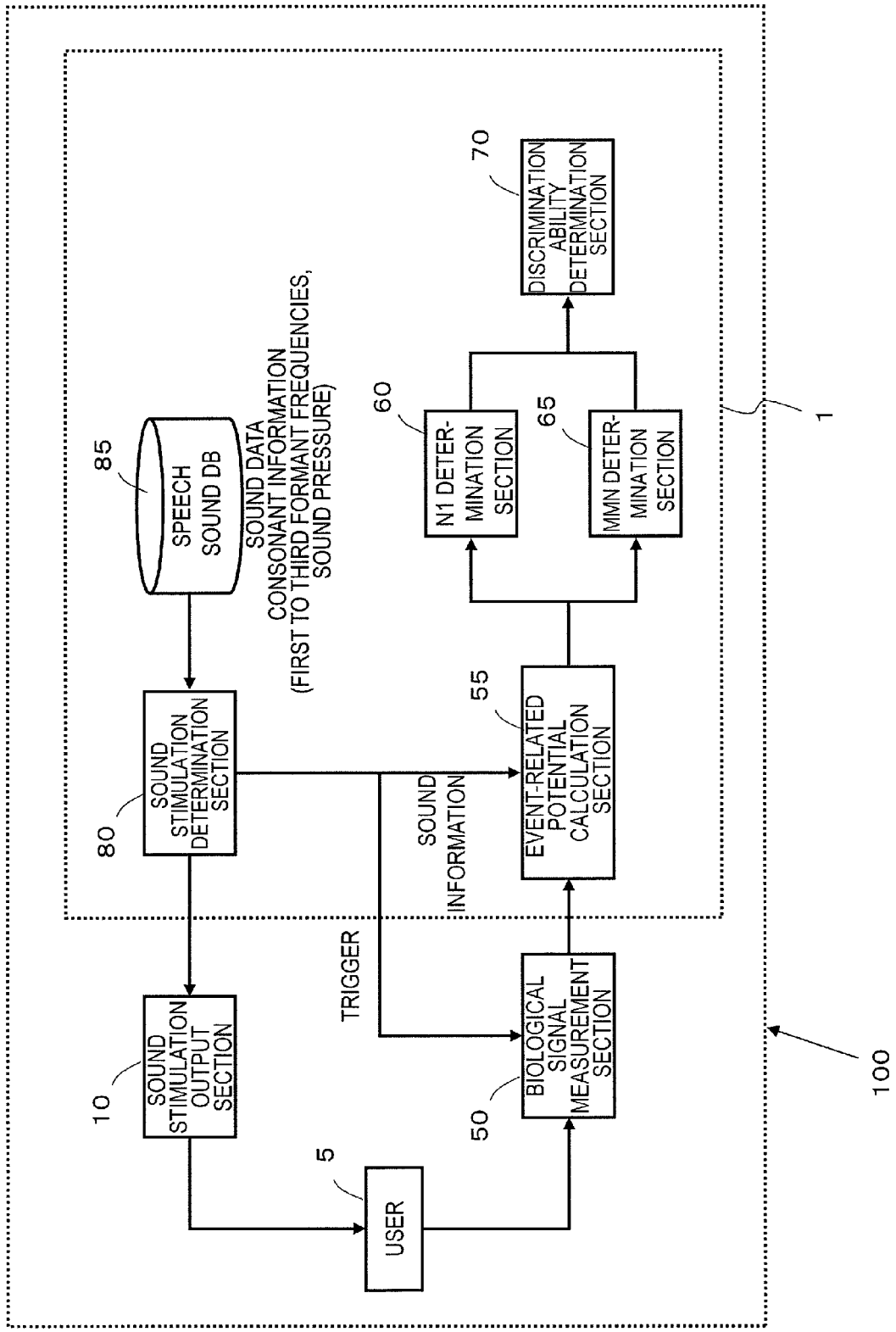
FIG. 6 is a diagram showing the construction of an implementation of a speech discrimination ability determination system according to Embodiment 1.

FIG. 6 shows the functional block construction of a speech discrimination ability determination system 100 according to the present embodiment.

The speech discrimination ability determination system 100 includes a sound stimulation output section 10, a biological signal measurement section 50, and a speech discrimination ability determination apparatus 1. The speech discrimination ability determination apparatus 1 (hereinafter abbreviated as the "determination apparatus 1") includes an event-related potential acquisition section 55, an N1 determination section 60, an MMN determination section 65, a discrimination ability determination section 70, a sound stimulation determination section 80, and a speech sound database (DB) 85. The user 5 block is shown for convenience of explanation.

The determination apparatus 1 is connected to the sound stimulation output section 10 and the biological signal measurement section 50 in a wired or wireless manner.

To the user 5, the speech discrimination ability determination system 100 presents two or more kinds of speech sounds as sound stimulations to be subjected to speech discrimination ability determination. Based on the presence or absence of an N1 component in the ERP corresponding to each sound stimulation, it is determined whether the sound stimulation is audible to the user 5 or not, and based on the presence or absence of an MMN component, it is determined whether the user discriminates the sound stimulations or not. The respective component elements will be described in detail later.

The determination apparatus 1 may at least include the event-related potential acquisition section 55, the N1 determination section 60, the MMN determination section 65, and the discrimination ability determination section 70. By using the information of the sound stimulations which are output from the sound stimulation output section 10, the event-related potential acquisition section 55 calculates an event-related potential from the electroencephalogram received from the biological signal measurement section 50.

<Environment of Use>

Figure 7:
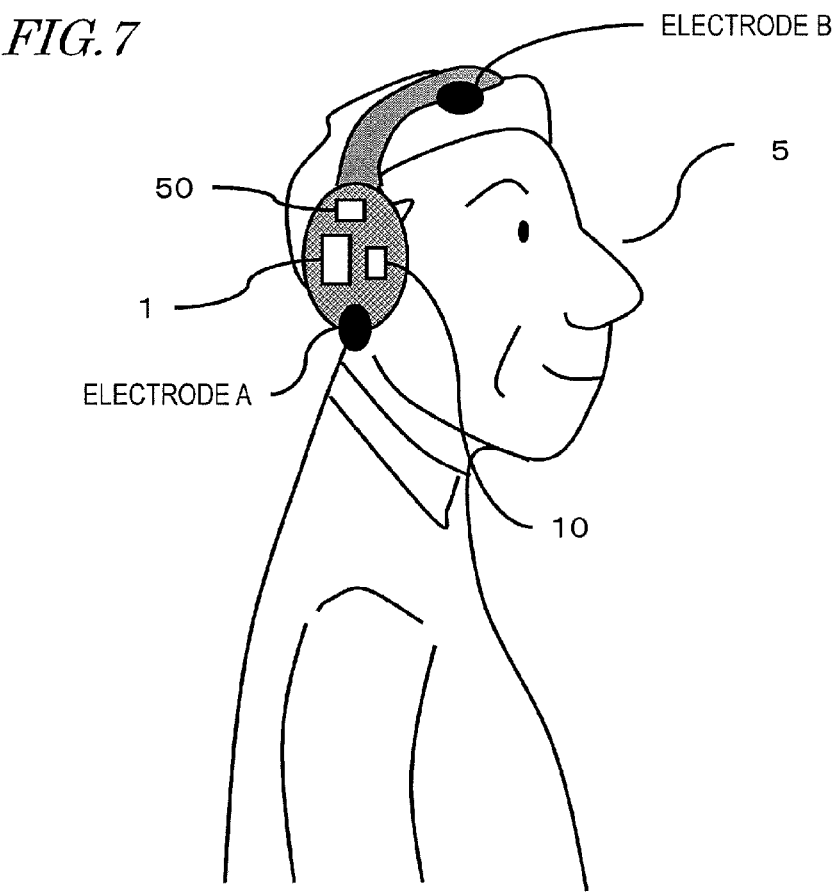
FIG. 7 is a diagram showing an environment of use for a speech discrimination ability determination system.

FIG. 7 shows an exemplary construction and environment of use for the speech discrimination ability determination system 100 of the present embodiment. The speech discrimination ability determination system 100 corresponds to the system construction of Embodiment 1 shown in FIG. 6.

The speech discrimination ability determination system 100 includes the determination apparatus 1, the sound stimulation output section 10, and the biological signal measurement section 50.

Although the determination apparatus 1 shown in FIG. 7 includes the biological signal measurement section 50 and the sound stimulation output section 10 in the same housing, the determination apparatus 1 may include the biological signal measurement section 50 and the sound stimulation output section 10 in separate housings. In that case, the biological signal measurement section 50 would send a measured electroencephalogram signal to the determination apparatus 1 being connected in a wireless or wired manner.

<Speech Discrimination Ability Determination Apparatus 1 (Determination Apparatus 1)>

The determination apparatus 1 determines information of sound stimulations to be output to the user 5.

The determination apparatus 1 determines the speech sound, and presentation timing, of a sound stimulation for speech discrimination ability determination. The sound stimulation output section 10 presents the sound stimulation which has been determined by the determination apparatus 1 to the user 5.

Moreover, from an event-related potential which has been cut out based on the sound stimulation as a starting point, an N1 component and an MMN component are extracted as characteristic amounts for determining a speech discrimination ability, and their presence or absence is determined. Then, from the presence or absence of an N1 component and an MMN component, it is determined whether there exists discrimination ability concerning the at least two or more kinds of sound stimulations that have been presented.

<Hardware Construction of the Determination Apparatus 1>

Figure 8:
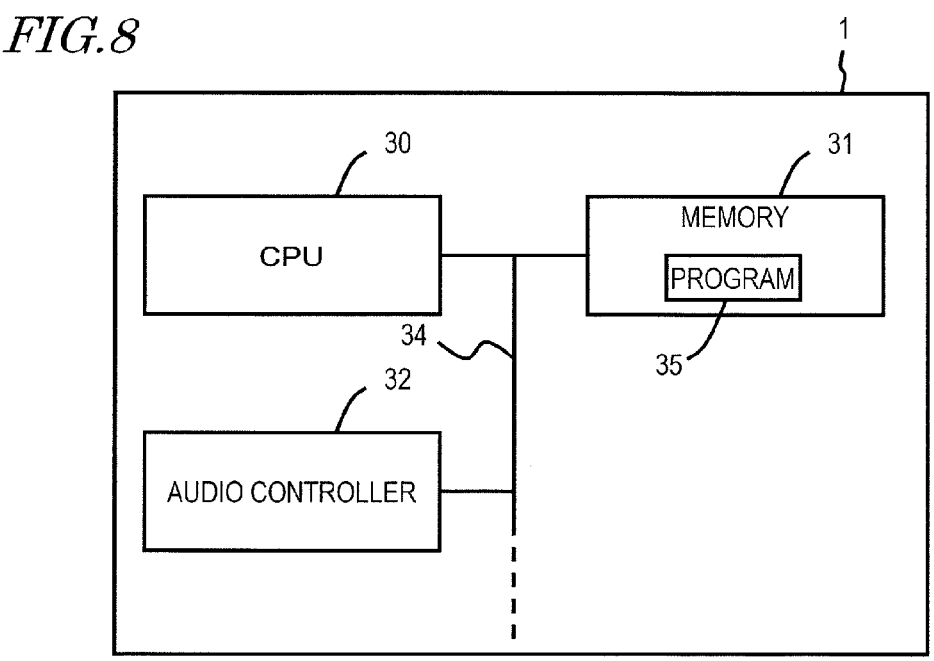
FIG. 8 is a diagram showing a hardware construction according to Embodiment 1.

FIG. 8 shows the hardware construction of the determination apparatus 1 of the present embodiment. The determination apparatus 1 includes a CPU 30, a memory 31, and an audio controller 32. The CPU 30, the memory 31, and the audio controller 32 are interconnected via a bus 34, so that data exchange among them is possible.

The CPU 30 executes a computer program 35 which is stored in the memory 31. A processing procedure as illustrated by a subsequently-described flowchart is described in the computer program 35.

In accordance with the computer program 35, the determination apparatus 1 performs processes of controlling the entire speech discrimination ability determination system 100, such as presentation of sound stimulations, extraction of characteristic amounts of event-related potential, speech discrimination ability determination, and hearing aid gain determination, by utilizing a speech sound DB 85 which is stored in the same memory 31.

In accordance with instructions from the CPU 30, the audio controller 32 outputs each sound stimulation to be presented with predetermined timing, via the sound stimulation output section 10.

Note that the determination apparatus 1 may be implemented as a piece of hardware (e.g., a DSP) consisting of a semiconductor circuit having a computer program incorporated therein. Such a DSP can realize all functions of the aforementioned CPU 30, memory 31, and audio controller 32 on a single integrated circuit.

The aforementioned computer program 35 may be distributed on the market in the form of a product recorded on a storage medium such as a CD-ROM or a flash memory, or transmitted through telecommunication lines such as the Internet. Upon reading the computer program 35, a device having the hardware shown in FIG. 8 (e.g., a PC) is able to function as the determination apparatus 1 according to the present embodiment.

Note that the speech sound DB 85 may not be retained in the memory 31, but may be stored on a hard disk (not shown) which is connected to the bus 34, for example.

The respective functional blocks of the determination apparatus 1 correspond to functions which are realized by the CPU 30, the memory 31, and the audio controller 32 as a whole upon executing the program which has been described in conjunction with FIG. 8.

Hereinafter, the respective component elements of the speech discrimination ability determination system 100 will be described.

<Speech Sound DB 85>

The speech sound DB 85 retains information of two or more kinds of speech sounds. The speech sound DB 85 at least retains information of kinds of speech sounds.

FIG. 9 shows an example of information which is retained in the speech sound DB 85 in the case where /g/ and /d/ are used as sound stimulations. The sound stimulations retained by the speech sound DB 85 include a consonant alone, a sound composed of a consonant and a transient state from the consonant to a vowel, an entire speech sound composed of a consonant and a vowel, and a sound in a predetermined time range from the rise of a consonant.

For each kind of speech sound ("ga" and "da"), the speech sound DB 85 shown in FIG. 9 retains an audio file and a consonant label. The audio file data may be a consonant alone, a sound composed of a consonant and a transient state from the consonant to a vowel, an entire speech sound composed of a consonant and a vowel, or a sound in a predetermined time range from the rise of a consonant.

The audio file is an audio signal of a speech sound. For example, the sound stimulation output section 10 (described later) reproduces the audio signal to present a sound stimulation. The audio file may contain audio information from the beginning of a consonant to the beginning of a vowel. For example, the audio file may be a standard-type test audio, or the audio file may be a recorded audio containing the voice of a person with whom conversations will mainly take place when a hearing aid is worn.

It is desirable that the audio file is an audio signal of a length of 25 ms or more, which is likely to induce an N1 component. Note that, so long as there are two or more of them, the kinds of speech sounds to be stored may not be limited to be within a confusable group; audio files of a plurality of groups which are likely to induce confusion may be stored.

Note that the determination apparatus 1 does not need to include the speech sound DB 85 as a component element. The speech sound DB 85 may be provided as a database on a network, for example. The determination apparatus 1 may wirelessly send or receive speech sound information in the speech sound DB 85 provided on a network.

<Sound Stimulation Determination Section 80>

By referring to the speech sound DB 85, the sound stimulation determination section 80 determines sound stimulation information containing a plurality of speech sounds. Examples of plurality of speech sounds will be represented as a first speech sound (speech sound A) and a second speech sound (speech sound B).

The sound stimulation information may contain the kinds of speech sounds to be presented, the occurrence frequencies with which the plurality of speech sounds are to be presented, an ear to which the sound stimulations are to be presented (the right ear or the left ear), and the timing of presenting the sound stimulations. The sound stimulation information at least contains information of the kinds of speech sounds to be presented.

It is desirable that the kinds of speech sounds are selected from within a range in which speech discrimination ability is to be determined. For example, in the case of determining the discrimination ability as to voiced plosive/affricative/fricative (b/d/g group), which are likely to cause confusion to a person with sensorineural hearing loss, speech sound b and speech sound d may be selected from within the group, for example.

The occurrence frequencies of the sound stimulations are to be set so that a difference in occurrence frequency exists between the standard stimulation and the deviant stimulation, e.g., 80% for the standard stimulation and 20% for the deviant stimulation. The standard stimulation may be any stimulation having an occurrence frequency which is at least greater than that of the deviant stimulation. Hereinafter, the occurrence frequency of the standard stimulation may also be referred to as the "first occurrence frequency", and the occurrence frequency of the deviant stimulation as the "second occurrence frequency". The first occurrence frequency has a predetermined range, and the second occurrence frequency has a range which is smaller than the predetermined range of the first occurrence frequency. For example, the first occurrence frequency may be between 51% and 99%, and the second occurrence frequency may be between 1% and 49%.

The standard stimulation and the deviant stimulation are switched for every trial block. For example, if speech sound b is the standard stimulation and speech sound d is the deviant stimulation in the first trial block, then speech sound d is the standard stimulation and speech sound b is the deviant stimulation in the second trial block.

Switching between the first trial block and the second trial block may be made at the timing when the deviant stimulation reaches a predetermined number of summations, or after the determination of the presence or absence of an N1 component and the presence or absence of an MMN component (described later) has begun to produce stable results, for example.

The predetermined number of times may be set to 150 times, for example.

The sound stimulations are presented to the ear of which discrimination ability is to be determined. In the case where determination is to be made for both ears, they are presented to both ears. The presentation timing is set in a range of 250 ms or more, so that the interval between sound stimulations will be longer than the latency of the MMN component. For example, it may be set so that the interval between sound stimulations is 500 ms.

The sound stimulations which are determined by the sound stimulation determination section 80 are output to the user 5 by the sound stimulation output section 10. At the timing with which a sound stimulation is output, the sound stimulation determination section 80 outputs a trigger signal to the biological signal measurement section 50. The timing that a sound stimulation is output is the point in time at which its consonant rises.

The sound stimulation information may be sent to the event-related potential acquisition section 55. The sound stimulation information contains the kind of sound stimulation presented, and information concerning the standard stimulation or the deviant stimulation. Note that the sound stimulation determination section 80 may only send generated sound stimulation data to the sound stimulation output section 10.

Note that the sound stimulation determination section 80 does not need to have a function of determining sound stimulations by itself. For example, it may be able to receive sound stimulation information via an input device not shown. For example, information which has been input by the user 5 or a person who tests the hearing of the user 5 may be adopted as the sound stimulation information.

In other words, the determination apparatus 1 would be able to function even if the sound stimulation determination section 80 and the speech sound DB 85 did not exist.

<Sound Stimulation Output Section 10>

The sound stimulation output section 10 outputs a speech sound determined by the sound stimulation determination section 80 to the user 5. Each speech sound that is output from the sound stimulation output section 10 includes a consonant alone, a sound composed of a consonant and a transient state from the consonant to a vowel, an entire speech sound composed of a consonant and a vowel, or a sound in a predetermined time range from the rise of a consonant.

Note that the electroencephalogram signal contains various information concerning e.g., the cerebral process of the user 5 with respect to stimulations. Generally speaking, vowels have larger sound pressure than do consonants, and thus there is a possibility that event-related potential that is induced by vowels or the like may be contained. When an MMN component is acquired from the electroencephalogram signal, other event-related potential components may exert influences. Therefore, by outputting a sound stimulation not including a vowel (e.g., a consonant alone, a sound composed of a consonant and a transient state from the consonant to a vowel, or a sound in a predetermined time range from the rise), there emerges a possibility that influences of any other event-related potential may be reduced.

Moreover, by reducing the time of each sound stimulation, the time required for speech discrimination ability determination can be reduced.

The sound stimulation output section 10 outputs the determined speech sounds at least through separation between the first trial block and the second trial block. In the first trial block, the first speech sound is output as the standard stimulation, and the second speech sound is output as the deviant stimulation. In the second trial block, the second speech sound is output as the standard stimulation, and the first speech sound is output as the deviant stimulation.

It is preferable that the first occurrence frequency and second occurrence frequency in the first trial block and the first occurrence frequency and second occurrence frequency in the second trial block are equal; however, they do not need to be equal.

For example, the sound stimulation output section 10 reproduces sound stimulation data which is received from the sound stimulation determination section 80 for presentation to the user 5. Alternatively, the sound stimulation output section 10 may externally acquire sound stimulation data that corresponds to the speech sounds determined by the sound stimulation determination section 80, for presentation to the user 5.

The sound stimulation output section 10 may be headphones in the case of determining speech discrimination ability as to either the right or left only, or may be a speaker set in the case of determining speech discrimination ability for both ears, for example. It is desirable to present any speech sound determined by the sound stimulation determination section 80 to the user 5 without allowing its frequency characteristics to be distorted.

<Biological Signal Measurement Section 50>

The biological signal measurement section 50 is an electroencephalograph which measures a biological signal of the user 5.

The biological signal measurement section 50 measures an electroencephalogram corresponding to a potential difference between a probe electrode and a reference electrode attached on the user 5.

Figure 11A:
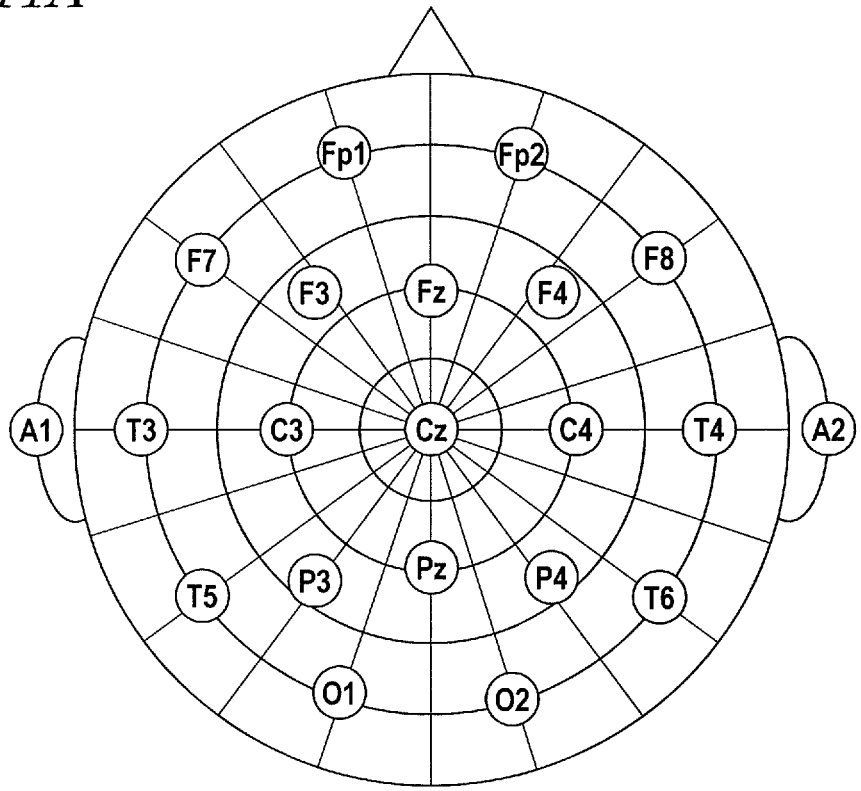
FIGS. 11A and 11B are diagrams showing electrode positioning.
Figure 11B:
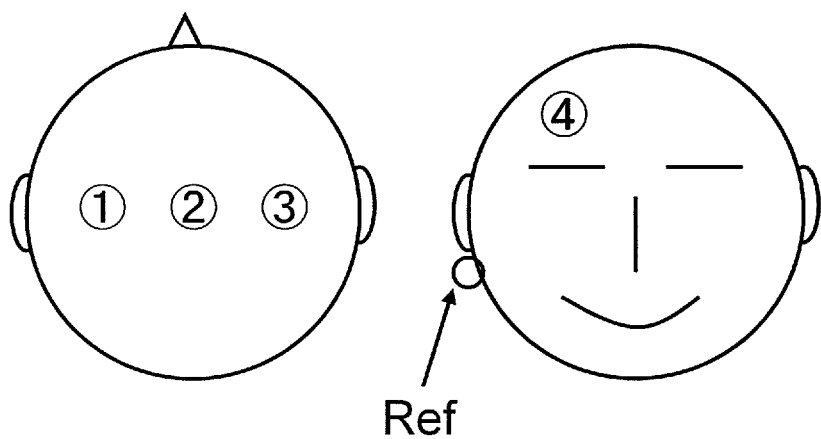

The probe electrode is set at an electrode position according to the International 10-20 system shown in FIG. 11A, for example. The probe electrode is set to the central portion Cz, or the sinciput Fz, for example. The reference electrode is placed at a mastoid of the user 5, for example.

Note that the level (amplitude level) and polarity (the amplitude being plus or minus) of a characteristic component of the event-related potential may possibly vary depending on the sites at which electrodes for electroencephalogram measurement are worn, and on the positions at which the reference electrode and the probe electrode are set.

However, based on the following description, those skilled in the art should be able to extract a characteristic feature of the event-related potential and perform a speech discrimination ability determination by making appropriate modifications in accordance with the particular reference electrode and probe electrode used. Such variants are encompassed within the present invention.

The electroencephalogram data may be subjected to frequency filtering with an appropriate cutoff frequency. The biological signal measurement section 50 sends the measured electroencephalogram or filtered electroencephalogram to the determination apparatus 1 (event-related potential acquisition section 55). Hereinafter, information of a measured or filtered electroencephalogram may also be referred to as "electroencephalogram data".

The electroencephalogram data contains event-related potential. Event-related potential means a change in electroencephalogram potential that occurs in response to a given stimulation. For example, the type of an event-related potential signal is determined based on (1) the polarity (positive or negative) of potential, (2) latency (the time since a stimulation until potential is induced), (3) the amplitude level of the potential, and so on.

For example, the electroencephalogram data is subjected to frequency filtering with an appropriate cutoff frequency, and based on a trigger received from the determination apparatus 1 (sound stimulation determination section 80) as a starting point, an event-related potential in a predetermined zone is cut out, and this waveform data (event-related potential) is sent to the event-related potential acquisition section 55. The predetermined zone is a zone including 0 ms, based on the trigger as a starting point, to 250 ms, at which an MMN component would be induced: e.g., a zone from 100 ms before the trigger to 500 ms after the trigger. The trigger may be the point in time at which a consonant rises, for example.

In the case where a band-pass filter is used as the frequency filter, the cutoff frequency may be set so as to pass e.g. 0.5 Hz to 20 Hz. It is assumed that the user 5 has worn the electroencephalograph in advance.

<Event-Related Potential Acquisition Section 55>

In accordance with the information of sound stimulations which has been output from the sound stimulation output section 10, the event-related potential acquisition section 55 acquires an event-related potential from the electroencephalogram (event-related potential) received from the biological signal measurement section 50. The sound stimulation information may be received from the sound stimulation determination section 80, or from the sound stimulation output section 10.

The event-related potential acquisition section 55 acquires an event-related potential for each of the standard stimulation and the deviant stimulation, and for each speech sound constituting a sound stimulation. Alternatively, the event-related potential acquisition section 55 may acquire an event-related potential for each speech sound constituting a sound stimulation, irrespective of the standard stimulation or the deviant stimulation.

For instance, the following six are possible methods of event-related potential calculation:

(1) irrespective of standard/deviant, obtain event-related potential as an arithmetic mean of ERP corresponding to all speech sounds A;

(2) irrespective of standard/deviant, obtain event-related potential as an arithmetic mean of ERP corresponding to all speech sounds B;

(3) obtain event-related potential as an arithmetic mean of ERP corresponding to speech sounds A as standard stimulations;

(4) obtain event-related potential as an arithmetic mean of ERP corresponding to speech sounds B as deviant stimulations;

(5) obtain event-related potential as an arithmetic mean of ERP corresponding to speech sounds B as standard stimulations; and (6) obtain event-related potential as an arithmetic mean of ERP corresponding to speech sounds A as deviant stimulations.

The event-related potential acquisition section 55 sends event-related potentials (1) and (2) to the N1 determination section 60, and sends event-related potentials (3) to (6) to the MMN determination section 65.

<N1 Determination Section 60>

From the event-related potential acquisition section 55, the N1 determination section 60 receives an event-related potential for each kind of sound stimulation, irrespective of standard stimulation or deviant stimulation. Note that the N1 determination section 60 may receive an arithmetic-meaned event-related potential. From the received event-related potential, the N1 determination section 60 determines the presence or absence of an N1 component for each sound stimulation.

For example, the N1 determination section 60 determines the presence or absence of an N1 component based on whether or not a negative peak exists in the event-related potential in a time range from 50 ms to 150 ms after the sound stimulation.

If a negative peak exists, the presence of an N1 component is determined; if no negative peak exists, the absence of an N1 component is determined.

If a negative peak (negative peak potential) which is smaller than a predetermined threshold value exists, it is determined that a negative peak exists. On the other hand, if a negative peak with an amplitude greater than the predetermined threshold value exists, it is determined that no negative peak exists. Note that, in the case of using the amplitude of a negative component (i.e., the absolute value of a negative component) to determine the presence or absence of an N1 component, the presence or absence of an N1 component may be determined based on whether the absolute value of the amplitude of the negative component is greater than a predetermined criterion or not. For example, an N1 component may be determined as present when the absolute value of the amplitude of the negative component is equal to or greater than a predetermined criterion, and an N1 component may be determined as absent when the absolute value of the amplitude of the negative component is smaller than the predetermined criterion. Note that, when making an amplitude-based determination, it must be guaranteed that the electroencephalogram component is minus in the time range which is utilized for determination after the sound stimulation. Generally speaking, any electroencephalogram component in the aforementioned time range from 50 ms to 200 ms after a sound stimulation is minus. Thus, it is possible to use a negative peak value, or use the amplitude of a negative component.

The N1 determination section 60 determines the presence or absence of an N1 component by using the peak potential of a negative component, a zone average potential, or a similarity level with respect to a template or the like.

For example, a zone average potential around a latency of about 100 ms may be compared against a predetermined threshold value to determine the presence or absence of an N1 component. The zone average potential may be an average potential in a time range based on a latency of about 100 ms. The predetermined threshold value may be 0 μV, for example.

Moreover, the N1 determination section 60 may retain a template of a waveform having an N1 component or a waveform lacking an N1 component. The N1 determination section 60 may determine the presence or absence of an N1 component by comparing the similarity level between the received waveform and the template against a predetermined threshold value.

In the present specification, the "event-related potential which is equal to or less than a predetermined threshold value", which is utilized by the N1 determination section 60, encompasses: an event-related potential of which the peak potential of a negative component or a zone average potential in a time range based on a latency of about 100 ms is equal to or less than a predetermined criterion; an event-related potential of which the amplitude of a negative component in a time range based on a latency of about 100 ms is equal to or greater than a predetermined criterion; and an event-related potential whose similarity level with respect to a predetermined template is equal to or greater than a predetermined criterion. Moreover, an "event-related potential which is greater than the predetermined threshold value", which is utilized by the N1 determination section 60, encompasses: an event-related potential of which the peak potential of a negative component or a zone average potential in a time range based on a latency of about 100 ms is greater than the predetermined criterion; an event-related potential of which the amplitude of a negative component in a time range based on a latency of about 100 ms is smaller than the predetermined criterion; and an event-related potential whose similarity level with respect to a predetermined template is smaller than the predetermined criterion.

The result of determining the presence or absence of an N1 component is sent to the discrimination ability determination section 70. Note that the determination result as to the presence or absence of an N1 component may be a negative peak value, an average potential in a time range based on a latency of about 100 ms, or a similarity level with respect to a template, instead of information of the presence or absence of an N1 component.

<MMN Determination Section 65>

For each kind of sound stimulation received from the event-related potential acquisition section 55, the MMN determination section 65 acquires difference information of ERP corresponding to the standard stimulation from the ERP corresponding to the deviant stimulation. The difference information of event-related potential contains waveform information of event-related potential, and information of a potential value associated with latency.

When speech sound A and speech sound B are presented, for example, the MMN determination section 65 subtracts the ERP corresponding to speech sound A as the standard stimulation in Trial block A, from the ERP corresponding to speech sound A as the deviant stimulation in Trial block B.

The MMN determination section 65 makes a determination based on whether a negative component exists in a time range from 150 ms to 250 ms in latency of the subtraction waveform, specifically: that an MMN component is absent if the peak potential of a negative component around a latency of about 200 ms is greater than a predetermined criterion; or that an MMN component is present if the peak potential of a negative component around a latency of about 200 ms is equal to or less than the predetermined criterion.

In the case where the presence or absence of an MMN component is determined by using the absolute value of the amplitude of the negative component, the presence or absence of an MMN component may be determined based on whether the absolute value of the amplitude of the negative component is greater than a predetermined criterion or not. For example, it is determined that an MMN component is present if the absolute value of the amplitude of the negative component is equal to or greater than the predetermined criterion, and it is determined that an MMN component is absent if the absolute value of the amplitude of the negative component is smaller than the predetermined criterion.

Similarly to the N1 determination section 60, the MMN determination section 65 determines the presence or absence of an MMN component by using a negative component peak, a zone average potential, or a similarity level with respect to a template, as the value of a negative component around a latency of about 200 ms.

For example, a zone average potential over a period of time in latency from 100 ms to 250 ms may be calculated, and it may be determined that an MMN component is present if the zone average potential is equal to or less than a predetermined threshold value, or that an MMN component is absent if the zone average potential is greater than the predetermined threshold value. Herein, the predetermined threshold value may be 0 μV, for example.

In the present specification, the "event-related potential which is equal to or less than a predetermined threshold value", which is utilized by the MMN determination section 65, encompasses: an event-related potential of which the peak potential of a negative component or a zone average potential in a time range around a latency of about 200 ms is equal to or less than a predetermined criterion; an event-related potential of which the amplitude of a negative component in a time range around a latency of about 200 ms is equal to or greater than a predetermined criterion; and an event-related potential whose similarity level with respect to a predetermined template is equal to or greater than a predetermined criterion. Moreover, an "event-related potential which is greater than the predetermined threshold value", which is utilized by the MMN determination section 65, encompasses: an event-related potential of which the peak potential of a negative component or a zone average potential in a time range around a latency of about 200 ms is greater than the predetermined criterion; an event-related potential of which the amplitude of an negative component in a time range around a latency of about 200 ms is smaller than the predetermined criterion; and an event-related potential whose similarity level with respect to a predetermined template is smaller than the predetermined criterion.

When determining a discrimination ability with respect to two kinds of sound stimulations, there may be cases where an MMN component is determined as present for only one of them; in those cases, it may be determined that an MMN component is absent, and the determination that an MMN component is present may be made only if an MMN component is determined as present for all sound stimulations. The determination result as to the presence or absence of an MMN component is sent to the discrimination ability determination section 70.

Note that the test time may be extended if the determination as to an MMN component in the ERP corresponding to speech sound A is inconsistent with the determination as to an MMN component in the ERP corresponding to speech sound B.

The result of determining the presence or absence of an N1 component is sent to the discrimination ability determination section 70. Note that the determination result as to the presence or absence of an MMN component may be a negative peak value, an average potential in a time range based on a latency from 100 ms to 250 ms, or a template, instead of information of the presence or absence of an MMN component.

<Discrimination Ability Determination Section 70>

With reference to a predetermined determination criterion, the discrimination ability determination section determines a speech discrimination ability from the presence or absence of an N1 component as received from the N1 determination section 60, and the presence or absence of an MMN component as received from the MMN determination section 65.

FIG. 4 shows an exemplary predetermined determination criterion.

Specifically, the case where an N1 component has occurred for both speech sound A and speech sound B is determined as "present" in FIG. 4. The case where an N1 component has occurred for only either one of speech sound A and speech sound B is determined as "present for only one of them" in FIG. 4. The case where an N1 component has occurred for neither speech sound A nor speech sound B is determined as "absent" in FIG. 4.

Six examples of determination results of speech discrimination ability based on the presence or absence of an N1 component and on the presence or absence of an MMN component are shown below.

(1) If an N1 component has occurred for all speech sounds and an MMN component is present, it is determined that speech sound discrimination is correctly done. (2) If an N1 component has occurred for all speech sounds and an MMN component is absent, it is determined that they are heard but not discriminated. (3) If an N1 component has not occurred for either sound stimulation and an MMN component is present, it is determined that one of the consonant is not heard. (4) If an N1 component has not occurred for either sound stimulation and an MMN component is absent, it is determined that the electroencephalogram is not being properly measured. (5) If an N1 component has occurred for none of the sound stimulations and an MMN component is present, it is determined that the electroencephalogram is not being properly measured. (6) If an N1 component has occurred for none of the sound stimulations and an MMN component is absent, it is determined that none of the consonants is heard.

<Processing by the Speech Discrimination Ability Determination System 100>

Figure 10:
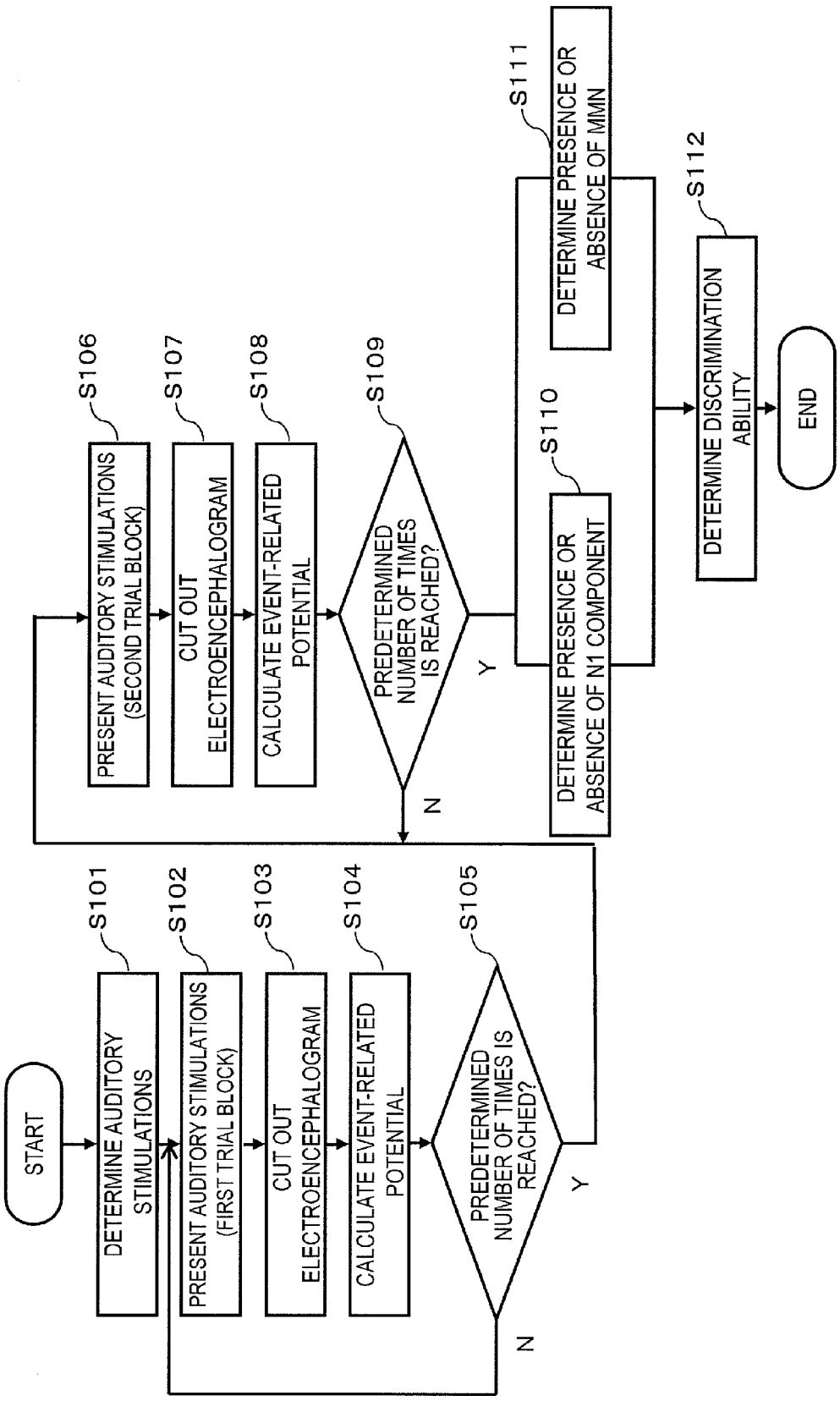
FIG. 10 is a flowchart showing overall processing by the speech discrimination ability determination system according to Embodiment 1 in outline.

Next, with reference to FIG. 10, a processing procedure by the speech discrimination ability determination system 100 of FIG. 6 will be described. FIG. 10 is a flowchart showing a procedure of processing by the speech discrimination ability determination system 100.

<Step S101>

By referring to the speech sound DB 85, the sound stimulation determination section 80 determines information of two or more kinds of sound stimulations to be presented to the user 5.

The sound stimulation information contains the kinds of speech sounds to be presented as sound stimulations, occurrence frequencies of the stimulations, the ear to which the sound stimulations are to be presented (the right ear or the left ear), and presentation timing. The sound stimulations include a consonant alone, a sound composed of a consonant and a transient state from the consonant to a vowel, an entire speech sound composed of a consonant and a vowel, and a sound in a predetermined time range from the rise of a consonant.

The kinds of speech sounds constituting the sound stimulations are selected from within a range in which speech discrimination ability is to be determined. For example, in the case of determining the discrimination ability as to voiced plosive/affricative/fricative (b/d/g group), which are likely to cause confusion to a person with sensorineural hearing loss, speech sound b and speech sound d are selected within the group, for example. The occurrence frequencies of the sound stimulations are set so that a difference in occurrence frequency exists between the standard stimulation and the deviant stimulation, e.g., 80% for the standard stimulation and 20% for the deviant stimulation.

<Step S102>

The sound stimulation output section 10 presents the first speech sound determined by the sound stimulation determination section 80 as sound stimulations to the user 5, with occurrence frequencies set for the first trial block.

For example, speech sound b is presented as the standard stimulation with an occurrence frequency of 80%, and speech sound d is presented as the deviant stimulation with an occurrence frequency of 20%. The sound stimulations are presented to the ear of which discrimination ability is to be determined. In the case where determination is to be made for both ears, they are presented to both ears. The presentation timing is set so that the interval between sound stimulations is 500 ms. Then, the sound stimulation determination section 80 outputs sound stimulations to the user 5 via the sound stimulation output section 10, and outputs trigger signals to the biological signal measurement section 50 at that timing. Also, it sends the particulars of the sound stimulations to the event-related potential acquisition section 55. Particulars of a sound stimulation are information concerning its consonant and it being standard or deviant.

<Step S103>

Based on each trigger of sound stimulation presentation timing which was output by the sound stimulation determination section 80 at step S102 and step S103 as a starting point, the biological signal measurement section 50 cuts out an electroencephalogram in a time range from −100 to 500 ms, for example. The biological signal measurement section 50 sends the electroencephalogram having been cut out to the event-related potential acquisition section 55. The electroencephalogram having been cut out may be not only an electroencephalogram in a predetermined time range, but also an electroencephalogram across an entire time range within which a predetermined time range is marked up.

<Step S104>

Based on the electroencephalogram for each sound stimulation received from the biological signal measurement section 50 and the information of sound stimulation particulars received from the sound stimulation determination section 80, the event-related potential acquisition section 55 takes an arithmetic mean of the electroencephalogram to calculate an event-related potential.

<Step S105>

The sound stimulation determination section 80 determines whether the deviant stimulation has reached a predetermined number of times. In the present embodiment, the predetermined number of times is 150 times, for example.

If the predetermined number of times has not been reached, the process returns to step S102; if it has been reached, the process proceeds to step S106.

<Step S106>

The sound stimulation output section 10 presents the second speech sounds determined by the sound stimulation determination section 80 as sound stimulations to the user 5, with occurrence frequencies set for the second trial block.

For example, speech sound d is presented as the standard stimulation with an occurrence frequency of 80%, and speech sound b is presented as the deviant stimulation with an occurrence frequency of 20%. Otherwise, this is similar to step S102.

<Steps S107 and S108>

The processes of steps S107 and S108 are respectively identical to the processes of steps S103 and S104, and the descriptions thereof are omitted.

<Step S109>

The sound stimulation determination section 80 determines whether the deviant stimulation has reached a predetermined number of times. In the present embodiment, the predetermined number of times is 150 times, for example.

If the predetermined number of times has not been reached, the process returns to step S106; if it has been reached, the process proceeds to steps S110 and S111.

In order to determine the presence or absence of and N1 component and an MMN component, the following six event-related potentials are separately calculated:

(1) irrespective of standard/deviant, obtain event-related potential as an arithmetic mean of ERP corresponding to all speech sounds A;

(2) irrespective of standard/deviant, obtain event-related potential as an arithmetic mean of ERP corresponding to all speech sounds B;

(3) obtain event-related potential as an arithmetic mean of ERP corresponding to speech sounds A as standard stimulations;

(4) obtain event-related potential as an arithmetic mean of ERP corresponding to speech sounds B as deviant stimulations;

(5) obtain event-related potential as an arithmetic mean of ERP corresponding to speech sounds B as standard stimulations; and (6) obtain event-related potential as an arithmetic mean of ERP corresponding to speech sounds A as deviant stimulations.

The event-related potential acquisition section 55 sends event-related potentials (1) and (2) to the N1 determination section 60, and event-related potentials (3) to (6) to the MMN determination section 65.

<Step S110>

Based on the event-related potential received from the event-related potential acquisition section 55, which has been arithmetic-meaned for each kind of sound stimulation irrespective of standard stimulation or deviant stimulation, the N1 determination section 60 determines the presence or absence of an N1 component for each sound stimulation.

Based on whether a negative peak exists in the event-related potential around a latency of about 100 ms, the determination of the presence or absence of an N1 component is done, wherein, if a negative peak exists, the presence of an N1 component is determined; if no negative peak exists, the absence of an N1 component is determined.

For example, a zone average potential around a latency of about 100 ms may be calculated, and a determination of the presence or absence of an N1 component may be made that: an N1 component is present if the zone average potential is smaller than a predetermined threshold value; or an N1 component is absent if it is greater than the predetermined threshold value. The predetermined threshold value may be 0 μV, for example. Then, the result of determining the presence or absence of an N1 component is sent to the discrimination ability determination section 70.

<Step S111>

For each kind of sound stimulation received from the event-related potential acquisition section 55, the MMN determination section 65 subtracts the response to the standard stimulation from that of the deviant stimulation.

For example, when speech sound A and speech sound B are presented, the response to speech sound A as the standard stimulation is subtracted from that of speech sound A as the deviant stimulation. Then, based on whether a negative component exists in the electroencephalogram in a time range from about 150 ms to 250 ms in latency of the subtraction waveform, an MMN component is determined as present if a negative component exists, and an MMN component is determined as absent if it does not exist.

When determining a discrimination ability with respect to two kinds of sound stimulations, there may be cases where an MMN component is determined as present for only one of them; in those cases, it may be determined that an MMN component is absent, and the determination that an MMN component is present may be made only if an MMN component is determined as present for all sound stimulations. The determination result as to the presence or absence of an MMN component is sent to the discrimination ability determination section 70.

<Step S112>

The discrimination ability determination section 70 determines a speech-sound discrimination ability, from the presence or absence of an N1 component and the presence or absence of an MMN component as received from the N1 determination section 60 and the MMN determination section 65.

Specifically, speech-sound discrimination ability is determined by using the determination criterion in FIG. 4 described above. When an N1 component is induced for all auditory stimulations, based on the presence or absence of an MMN component, a "correctly discriminated" determination is made if an MMN component is present, and a "heard but not discriminated" determination is made if an MMN component is absent. Moreover, if an N1 component has not been induced for either auditory stimulation but an MMN component is present, then it is determined that one of the consonant is not heard. If an N1 component has been induced for none of the auditory stimulations and an MMN component is absent, it is determined that none of the consonants is heard. If an N1 component has not been induced for either consonant and an MMN component is absent, and also if an N1 component has been induced for none of the auditory stimulations but an MMN component is present, it is determined that the electroencephalogram is not being properly measured. In this case, electroencephalogram measurement may be repeated until any other determination result is obtained. Then, the result of discrimination ability determination is retained in a non-volatile memory (not shown), for example. Alternatively, the determination apparatus 1 may output the result of discrimination ability determination to an external device. The external device would be able to determine the gain of a hearing aid by using the determination result.

With the speech discrimination ability determination system 100 of the present embodiment, two or more kinds of speech sounds, from the beginning of a consonant and inclusive of a transient state until the beginning of a vowel, are presented as sound stimulations, with a difference in occurrence frequency therebetween, and based on the presence or absence of and N1 component and an MMN component in the ERP corresponding to the sound stimulations, speech discrimination ability is determined. As a result, a speech discrimination ability determination can be made with a high precision.

In the description of the present embodiment, it is illustrated that the biological signal measurement section 50 cuts out an event-related potential in a predetermined range based on a trigger from the sound stimulation determination section 80 as a starting point, and sends it to the event-related potential acquisition section 55. However, this process is an example. In another process, for example, the biological signal measurement section 50 may constantly be measuring electroencephalogram, while the event-related potential acquisition section 55 may cut out any necessary event-related potential and apply a baseline correction thereto. With such construction, the sound stimulation determination section 80 does not need to send a trigger to the biological signal measurement section 50, but may send a trigger to the event-related potential acquisition section 55.

Variant of Embodiment 1

In Embodiment 1, the presence or absence of an N1 component is determined while expecting that sound stimulations may not be heard by the user in some cases. The presence of an N1 component is regarded as indicating that a sound stimulation is audible, then followed by an MMN component determination process.

Also expectable are, certainly, cases where sound stimulations are previously known to be perceivable. It is guaranteed in those cases that no missing stimulations exist, and thus it may be said that there is no need to determine the presence or absence of an N1 component. A guarantee that there exist no missing stimulations may be obtained by confirming through advance subjective reporting as to whether sound stimulations are audible or not, for example, to know for sure that all sound stimulations are audible.

Accordingly, a possible variant of Embodiment 1 is a speech discrimination ability determination system lacking the N1 determination section 60.

Figure 12:
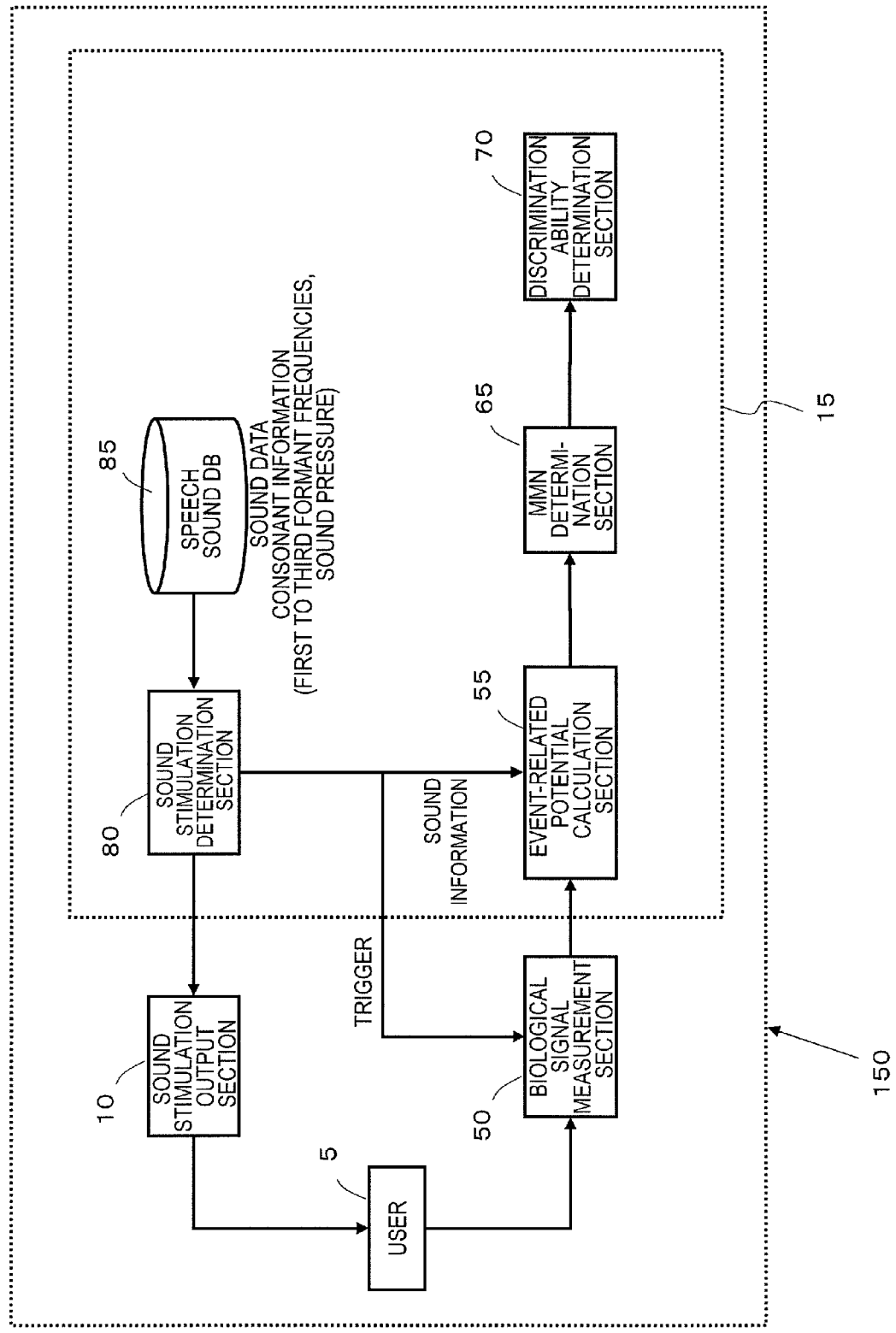
FIG. 12 is a diagram showing the construction of a speech discrimination ability determination system 150 lacking an N1 determination section.

FIG. 12 shows the construction of a speech discrimination ability determination system 150, from which the N1 determination section 60 is omitted. In the speech discrimination ability determination system 150, the discrimination ability determination section 70 determines a speech discrimination ability based on the presence or absence of an MMN component as determined by the MMN determination section 65 and on the determination criterion shown in FIG. 3.

The speech discrimination ability determination apparatus 15 may at least include the event-related potential acquisition section 55, the MMN determination section 65, and the discrimination ability determination section 70. As has been described in connection with Embodiment 1, the sound stimulation determination section 80 and the speech sound DB 85 may not be essential.

The procedure of processing by the speech discrimination ability determination apparatus 15 is realized through steps S101 to S112 in FIG. 10, excluding step S110.

Embodiment 2

In order to provide an improved discrimination ability, a speech discrimination ability determination system 200 according to Embodiment 2 determines how to adjust the gain of a hearing aid for each frequency, from a result of speech discrimination ability determination.

In addition to speech discrimination ability determination, the speech discrimination ability determination system 200 of Embodiment 2 utilizes formant frequencies and intensities of sound stimulations, and determines a hearing aid gain for each frequency, corresponding to a predetermined input sound pressure.

In accordance with a result of speech discrimination ability determination based on the presence or absence of and N1 component and an MMN component, when it is determined that speech discrimination ability is lacking, the speech discrimination ability determination system 200 of the present embodiment adjusts the gain of a hearing aid at a frequency that is related to a formant of a speech sound which has been presented as a sound stimulation.

Figure 13:
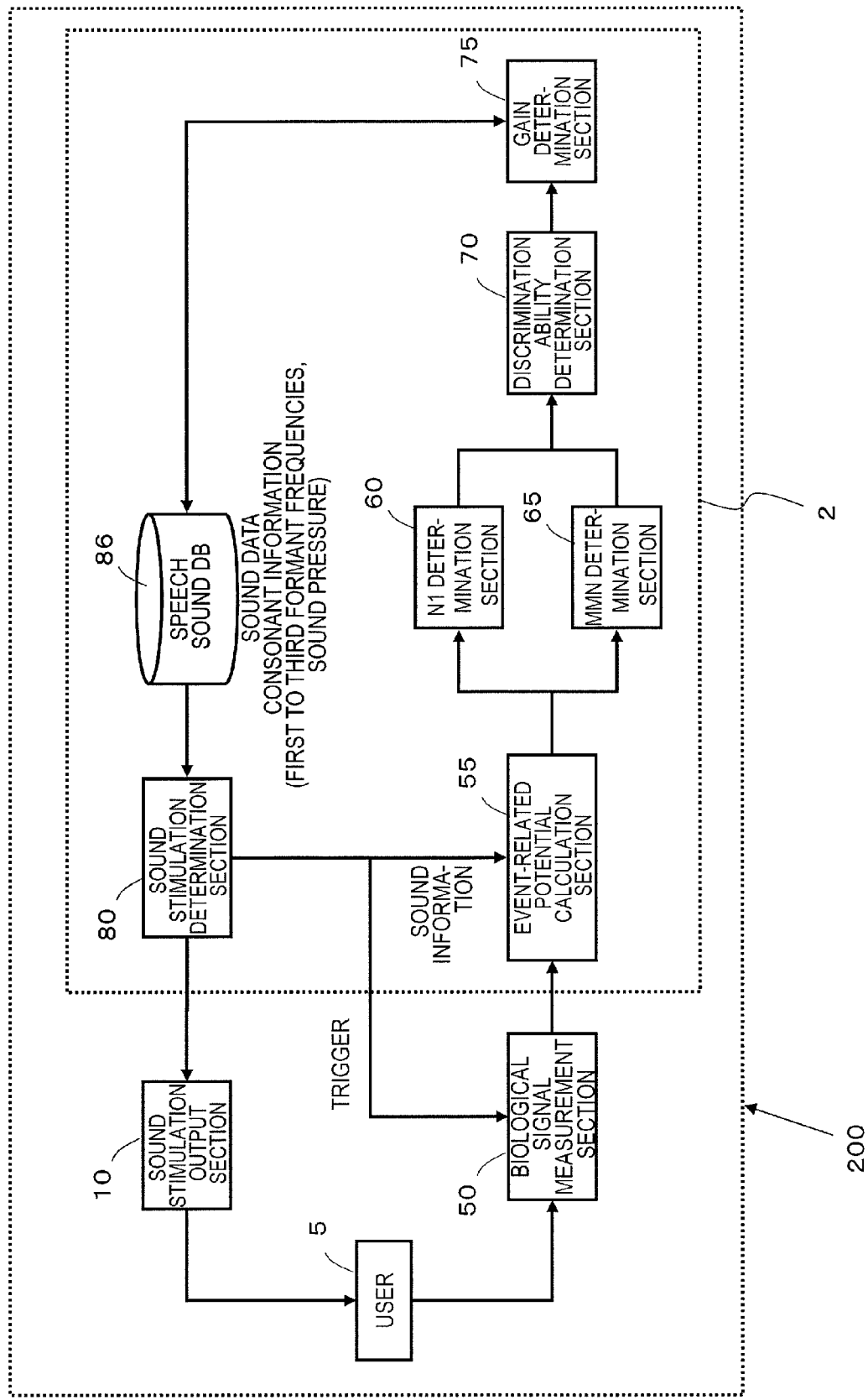
FIG. 13 is a diagram showing the construction of an implementation of a speech discrimination ability determination system according to Embodiment 2.

FIG. 13 shows the functional block construction of the speech discrimination ability determination system 200 of the present embodiment.

The speech discrimination ability determination system 200 includes the sound stimulation output section 10, the biological signal measurement section 50, and a hearing aid gain determination apparatus 2. Hereinafter, the hearing aid gain determination apparatus 2 will be abbreviated as the "determination apparatus 2". Blocks identical to those in FIG. 6 will be denoted by identical numerals, with their description omitted. Note that the determination apparatus 2 has a hardware construction as shown in FIG. 8. The determination apparatus 2 according to the present embodiment as shown in FIG. 13 is implemented as a result of executing a program defining different processes from those of the program 35 (FIG. 8).

The determination apparatus 2 according to the present embodiment differs from the determination apparatus 1 according to Embodiment 1 in that a speech sound DB 86 is provided instead of the speech sound DB 85, and a gain determination section 75 is newly introduced.

Hereinafter, the speech sound DB 86 and the gain determination section 75 will be described.

<Speech Sound DB 86>

Similarly to the speech sound DB 85, the speech sound DB 86 is a database which retains information of two or more kinds of speech sounds to be presented as sound stimulations. FIG. 14 shows an exemplary speech sound DB 86 in the case where /g/ and /d/ are used as speech sounds to be tested, for example. One difference from the speech sound DB 85 is that frequency and intensity information of formants is retained for each speech sound.

A frequency of a formant of a sound stimulation is, for example, a numerical value that is determined by a peak value in the spectrum envelope of an audio file at a predetermined timing since the beginning of the sound data. For example, in order to determine the frequencies of the first to third formants, three peaks of the spectrum envelope may be ascertained in ascending order of frequency. Intensity is a sound pressure at the frequency of each formant, and is information that is measurable with a noise level meter which is capable of measuring a sound pressure at each frequency, for example.

<Gain Determination Section 75>

The gain determination section 75 receives a determination result concerning speech-sound discrimination ability from the discrimination ability determination section 70, and, by referring to a predetermined criterion, determines a gain for the hearing aid based on the determination result.

A "gain for a hearing aid" is an amount by which the hearing aid performs sound amplification for each sound pressure or frequency of a sound that is input to the hearing aid. For example, it is a difference between the sound pressure of a sound which is input to a hearing aid and the sound pressure of a sound which is output from the hearing aid.

More specifically, the gain determination section retains as the predetermined criterion the presence or absence of an MMN component and the presence or absence of an N1 component and a method of hearing aid gain determination, and determines a gain for the hearing aid.

As for the N1 component, rather than information on the presence or absence of an N1 component, a negative peak potential or amplitude value in a time range based on a latency of about 100 ms, an average potential in a time range based on a latency of about 100 ms, or a similarity level with respect to a template may be received.

When the user 5 does not discriminate speech sounds or does not hear speech sounds, the gain determination section 75 refers to the speech sound DB 85 to determine a gain corresponding to the formant frequency(s) and sound pressure of the speech sound.

For example, if a "heard but not discriminated" determination is made, an increase in gain may be decided for any frequency at which there exists a large formant frequency difference between sound stimulations. On the other hand, if it is determined that a sound stimulation is not heard, an increase in hearing aid gain at all frequencies may be decided irrespective of the formant frequency(s) of the sound stimulation. Then, the audio data and sound stimulation information in the speech sound DB 86 is rewritten so as to reflect the gain information having been determined.

For example, under formant conditions such as those in FIG. 14, if a "heard but not discriminated" determination is made concerning speech discrimination ability, then the audio data is rewritten so that the sound pressure is increased by 5 dB at 2500 Hz and 3000 Hz of the third formant, at which formant frequency difference exists between sound stimulations, and the intensity information of the respective third formant is increased by 5 dB. Rewriting of audio data is easily realized by performing a process using an equalizer function.

Next, with reference to the flowchart of FIG. 15, an overall procedure of processing by the speech discrimination ability determination system 200 will be described.

Figure 15:
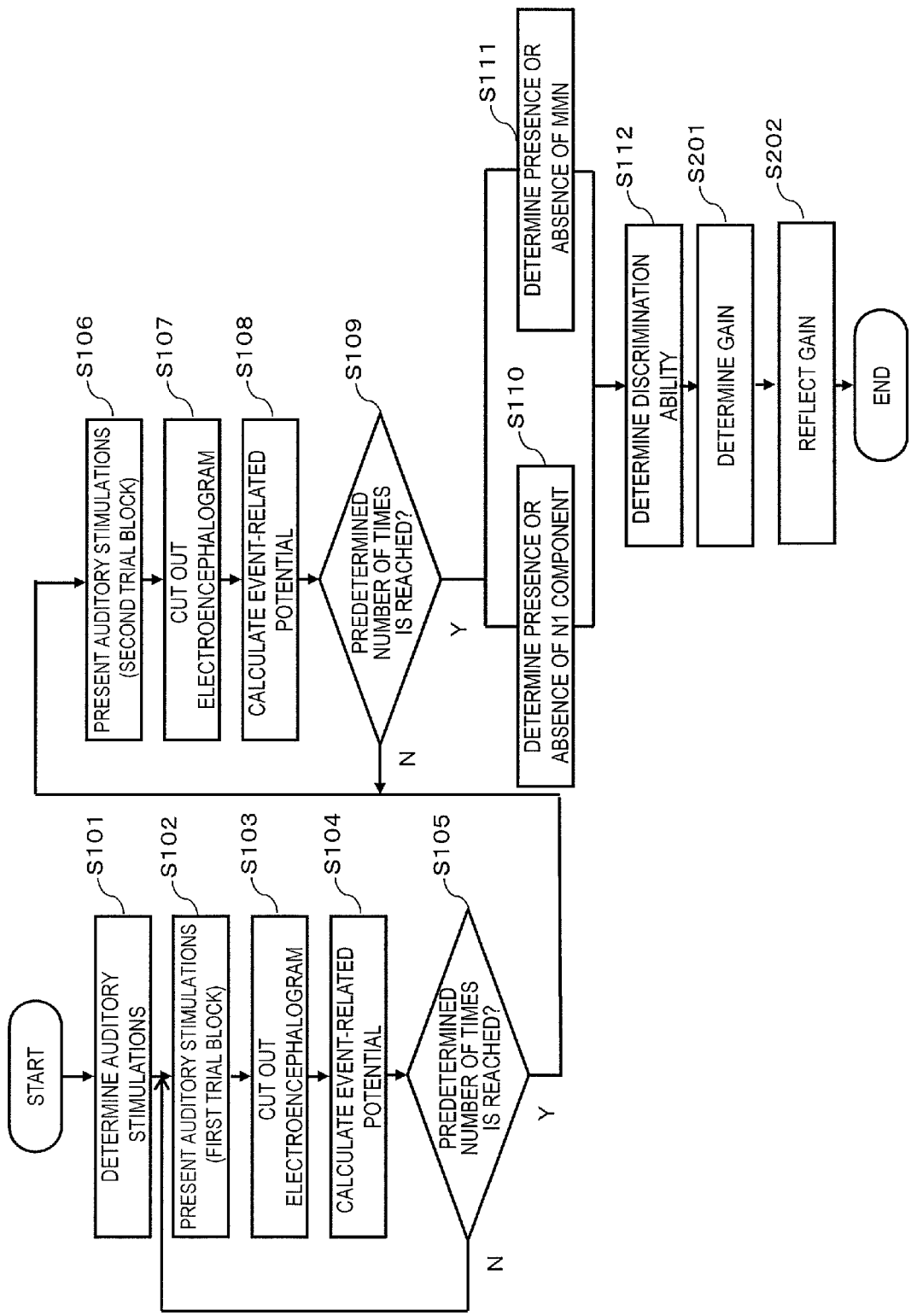
FIG. 15 is a flowchart showing overall processing by the speech discrimination ability determination system according to Embodiment 2 in outline.

FIG. 15 shows a processing procedure by the speech discrimination ability determination system 200 according to the present embodiment. In FIG. 15, steps at which identical processes to those of the processes of the speech discrimination ability determination system 100 (FIG. 10) are denoted by identical reference numerals, with their description omitted.

The processing by the speech discrimination ability determination system 200 according to the present embodiment differs from the processing by the speech discrimination ability determination system 100 according to Embodiment 1 (FIG. 10) in that step S201 to step S202 concerning gain determination and reflection are newly introduced.

<Step S201>

By referring to the predetermined criterion retained in the gain determination section 75, the gain determination section determines a gain for the hearing aid, based on the determination result by the discrimination ability determination section 70 concerning speech-sound discrimination ability.

For example, if the result of sound stimulation discrimination ability determination received from the discrimination ability determination section 70 indicates inability to discriminate or inability to hear the sound stimulation, the gain determination section 75 decides an increase in the gain for the formant frequency(s) and intensity of the sound stimulation, by referring to the speech sound DB 86.

For example, if a "heard but not discriminated" determination is made, an increase in hearing aid gain may be determined for any frequency at which there exists a large formant frequency difference between sound stimulations. On the other hand, if it is determined that a consonant is not heard, for example, an increase in hearing aid gain at all frequencies may be determined irrespective of the formant frequency(s) of the sound stimulation.

<Step S202>

The gain determination section 75 allows the gain determined at step S201 to be reflected in the speech sound DB 86.

Although the present embodiment illustrates that the gain determination section 75 updates the speech sound DB so as to reflect the determined gain, update is not necessary. The gain determination section 75 may store the determined gain. Moreover, the determined gain may be presented to a person who adjusts the hearing aid, and this person may use it for determining the gain of the hearing aid of the user 5.

With the speech discrimination ability determination system 200 of the present embodiment, two or more kinds of speech sounds, from the beginning of a consonant and inclusive of a transient state until the beginning of a vowel, are presented as sound stimulations, with a difference in occurrence frequency therebetween, and based on the presence or absence of and N1 component and an MMN component in the ERP corresponding to the sound stimulations, speech discrimination ability is determined. As a result, the speech discrimination ability of each user can be determined without requiring answer inputs, which would be cumbersome to the user. Then, if it is determined that speech discrimination ability is lacking, the gain at a frequency that is related to a formant of a speech sound which has been presented as a sound stimulation is determined. This provides information on a hearing aid fitting which provides more than satisfactory hearing while a hearing aid is worn.

Variant of Embodiment 2

As above, a speech discrimination ability determination system has been described as a variant of Embodiment 1, in which the determination apparatus 1 lacks the N1 determination section 60.

Similarly, as a variant of Embodiment 2, a hearing aid gain determination apparatus lacking an N1 determination section is conceivable.

Figure 17:
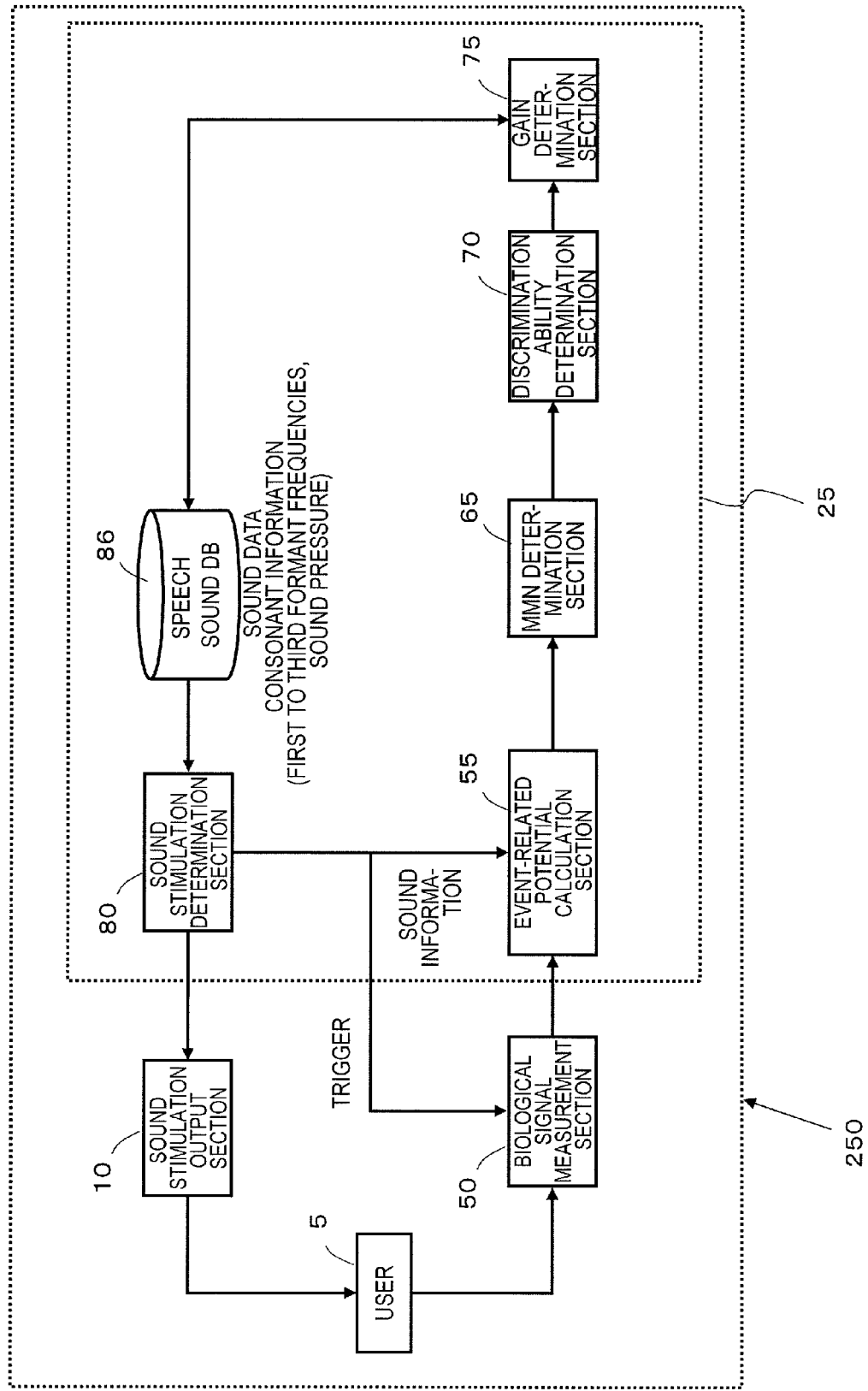
FIG. 17 is a diagram showing the construction of a speech discrimination ability determination system 250 lacking an N1 determination section.

FIG. 17 shows the construction of a speech discrimination ability determination system 250, from which the N1 determination section 60 is omitted. The hearing aid gain determination apparatus 25 of the speech discrimination ability determination system 250 may at least include the event-related potential acquisition section 55, the MMN determination section 65, and the gain determination section 75.

Based on the information of sound stimulations which is output from the sound stimulation output section 10, the event-related potential acquisition section 55 acquires an event-related potential from the biological signal measurement section 50.

The gain determination section 75 may retain as a predetermined criterion the presence or absence of an MMN component and a method of hearing aid gain determination, and determine a hearing aid gain based on the presence or absence of an MMN component by referring to the predetermined criterion.

Instead of information of the presence or absence of an MMN component, a negative peak potential or amplitude value in a time range from 150 ms to 250 ms in latency, an average potential in a time range from 150 ms to 250 ms in latency, or a similarity level with respect to a template may be received.

The gain determination section 75 may determine a hearing aid gain based on the amplitude value of a negative peak in a time range from 150 ms to 250 ms in latency, an average potential in a time range from 150 ms to 250 ms in latency, or a similarity level between a template and an electroencephalogram signal containing a waveform in a time range from 150 ms to 250 ms in latency.

The gain determination section 75 may determine a hearing aid gain based on a negative peak potential or amplitude value in a time range based on a latency of about 100 ms, an average potential in a time range based on a latency of about 100 ms, or a similarity level with respect to a template.

A speech discrimination ability determination system according to one implementation of the present invention allows a speech discrimination ability to be directly determined from the electroencephalogram of each user, and is useful for the adjustment of a hearing aid at a hearing aid shop or in households, etc.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A speech discrimination ability determination system comprising:
    a biological signal measurement section that measures an electroencephalogram signal of a user;
    a sound stimulation determination section that determines, by referring to a speech sound database storing information of a plurality of speech sounds, a first speech sound and a second speech sound which are different from each other;
    an output section that switches between: a first trial in which the first speech sound is output with a first occurrence frequency and the second speech sound is output with a second occurrence frequency different from the first occurrence frequency; and a second trial in which the first speech sound is output with the second occurrence frequency and the second speech sound is output with the first occurrence frequency;
    an event-related potential acquisition section that acquires an event-related potential contained in the electroencephalogram signal, the event-related potential acquisition section acquiring: an event-related potential based on a point of outputting the first speech sound being output with the first occurrence frequency as a starting point; an event-related potential based on a point of outputting the first speech sound being output with the second occurrence frequency as a starting point; an event-related potential based on a point of outputting the second speech sound being output with the first occurrence frequency as a starting point; and an event-related potential based on a point of outputting the second speech sound being output with the second occurrence frequency as a starting point;
    an MMN determination section that acquires, with respect to each of the first speech sound and the second speech sound, difference information between the event-related potential acquired during its output with the first occurrence frequency and the event-related potential acquired during its output with the second occurrence frequency, and configured to determine whether a negative component exists in the difference information in predetermined time ranges after the first speech sound and the second speech sound are output; and
    a discrimination ability determination section that determines that the user discriminates the first speech sound and the second speech sound when a determination result by the MMN determination section indicates that the negative component exists;
    wherein the output section outputs the first speech sound and the second speech sound with the first occurrence frequency being X (0<X<0.5) and the second occurrence frequency being (1−X).

2. The speech discrimination ability determination system of claim 1, wherein the MMN determination section determines that the negative component exists when determining that an event-related potential which is equal to or less than a predetermined threshold value exists in the difference information in the predetermined time ranges after the first speech sound and the second speech sound are output, and that the negative component does not exist when determining that an event-related potential which is greater than the predetermined threshold value exists.

3. The speech discrimination ability determination system of claim 1, wherein the predetermined time range is a time range from 100 ms to 250 ms.

4. The speech discrimination ability determination system of claim 3, further comprising
    an N1 determination section that determines whether an N1 component exists in a time range from 50 ms to 150 ms based on a point in time of outputting each of the first speech sound and the second speech sound as a starting point, the N1 component being a negative component of event-related potential, wherein,
    when a determination result by the N1 determination section indicates that the N1 component exists and the determination result by the MMN determination section indicates that the negative component exists, the discrimination ability determination section determines that the user discriminates the first speech sound and the second speech sound.

5. The speech discrimination ability determination system of claim 4, wherein the N1 determination section determines that the N1 component exists when determining that an event-related potential which is equal to or less than a predetermined threshold value exists in predetermined time ranges after the first speech sound and the second speech sound are output, and that the N1 component does not exist when determining that an event-related potential which is greater than the predetermined threshold value exists.

6. The speech discrimination ability determination system of claim 4, wherein, when the determination result by the N1 determination section indicates that the N1 component exists and the determination result by the MMN determination section indicates that the negative component does not exist, the discrimination ability determination section determines that the user hears the first speech sound and the second speech sound but does not discriminate between the first speech sound and the second speech sound.

7. The speech discrimination ability determination system of claim 3, further comprising
   an N1 determination section that determines whether an N1 component exists in a time range from 50 ms to 150 ms based on a point in time of outputting each of the first speech sound and the second speech sound as a starting point, the N1 component being a negative component of event-related potential, wherein,
   when a determination result by the N1 determination section indicates that the N1 component does not exist for either one of the first speech sound and the second speech sound and the determination result by the MMN determination section indicates that the negative component exists, the discrimination ability determination section determines that the user does not discriminate either one of the first speech sound and the second speech sound.

8. The speech discrimination ability determination system of claim 4, further comprising
   an N1 determination section that determines whether an N1 component exists in a time range from 50 ms to 150 ms based on a point in time of outputting each of the first speech sound and the second speech sound as a starting point, the N1 component being a negative component of event-related potential, wherein,
   when the determination result by the N1 determination section indicates that the N1 component exists for either one of the first speech sound and the second speech sound and the determination result by the MMN determination section indicates that the negative component does not exist, the discrimination ability determination section determines that the biological signal measurement section is not properly measuring the electroencephalogram signal.

9. The speech discrimination ability determination system of claim 4, further comprising
   an N1 determination section that determines whether an N1 component exists in a time range from 50 ms to 150 ms based on a point in time of outputting each of the first speech sound and the second speech sound as a starting point, the N1 component being a negative component of event-related potential, wherein,
   when the determination result by the N1 determination section indicates that the N1 component exists for neither the first speech sound nor the second speech sound and the determination result by the MMN determination section indicates that the negative component exists, the discrimination ability determination section determines that the biological signal measurement section is not properly measuring the electroencephalogram signal.

10. The speech discrimination ability determination system of claim 6, further comprising a gain determination section that decides an increase in a gain concerning a frequency at which a large formant frequency differences exists between the first speech sound and the second speech sound when the determination result by the discrimination ability determination section indicates that the user does discriminates neither the first speech sound nor the second speech sound.

11. The speech discrimination ability determination system of claim 7, comprising a gain determination section that decides an increase in gain across all audible frequencies when the determination result by the discrimination ability determination section indicates that the user hears neither the first speech sound nor the second speech sound.

12. The speech discrimination ability determination system of claim 1, wherein the output section performs the first trial, and after the number of times of outputting the first speech sound has reached a predetermined number of times, switches from the first trial to the second trial.

13. The speech discrimination ability determination system of claim 2, wherein the predetermined time range is a time range from 100 ms to 250 ms.

14. A speech discrimination ability determination apparatus for use in a speech discrimination ability determination system that switches between: a first trial in which a first speech sound is output with a first occurrence frequency and the second speech sound is output with a second occurrence frequency different from the first occurrence frequency; and a second trial in which the first speech sound is output with the second occurrence frequency and the second speech sound is output with the first occurrence frequency, comprising:
   an event-related potential acquisition section that acquires an event-related potential contained in an electroencephalogram signal measured by a biological signal measurement section, the event-related potential acquisition section acquiring: an event-related potential based on a point of outputting the first speech sound being output with the first occurrence frequency as a starting point; an event-related potential based on a point of outputting the first speech sound being output with the second occurrence frequency as a starting point; an event-related potential based on a point of outputting the second speech sound being output with the first occurrence frequency as a starting point; and an event-related potential based on a point of outputting the second speech sound being output with the second occurrence frequency as a starting point;
   an MMN determination section that acquires, with respect to each of the first speech sound and the second speech sound, difference information between the event-related potential acquired during its output with the first occurrence frequency and the event-related potential acquired during its output with the second occurrence frequency, and configured to determine whether a negative component exists in the difference information in predetermined time ranges after the first speech sound and the second speech sound are output; and
   a discrimination ability determination section that determines that the user discriminates the first speech sound and the second speech sound when a determination result by the MMN determination section indicates that the negative component exists;

wherein the first speech sound and the second speech sound are outputted with the first occurrence frequency being X (0<X<0.5) and the second occurrence frequency being (1−X).

15. A hearing aid gain determination apparatus for use in a speech discrimination ability determination system that switches between: a first trial in which a first speech sound is output with a first occurrence frequency and the second speech sound is output with a second occurrence frequency different from the first occurrence frequency; and a second trial in which the first speech sound is output with the second occurrence frequency and the second speech sound is output with the first occurrence frequency, comprising:

an event-related potential acquisition section that acquires an event-related potential contained in an electroencephalogram signal measured by a biological signal measurement section, the event-related potential acquisition section acquiring: an event-related potential based on a point of outputting the first speech sound being output with the first occurrence frequency as a starting point; an event-related potential based on a point of outputting the first speech sound being output with the second occurrence frequency as a starting point; an event-related potential based on a point of outputting the second speech sound being output with the first occurrence frequency as a starting point; and an event-related potential based on a point of outputting the second speech sound being output with the second occurrence frequency as a starting point;

an MMN determination section that acquires, with respect to each of the first speech sound and the second speech sound, difference information between the event-related potential acquired during its output with the first occurrence frequency and the event-related potential acquired during its output with the second occurrence frequency, and configured to determine whether a negative component exists in the difference information in predetermined time ranges after the first speech sound and the second speech sound are output;

a discrimination ability determination section that determines that the user discriminates the first speech sound and the second speech sound when a determination result by the MMN determination section indicates that the negative component exists; and a gain determination section that determines, by referring to a predetermined determination criterion, a gain for a hearing aid based on the difference information;

wherein the first speech sound and the second speech sound are outputted with the first occurrence frequency being X (0<X<0.5) and the second occurrence frequency being (1−X).

16. A speech discrimination ability determination method comprising:

by referring to a speech sound database storing information of a plurality of speech sounds, determining a first speech sound and a second speech sound which are different from each other;

measuring an electroencephalogram signal of a user;

performing a first trial in which the first speech sound is output with a first occurrence frequency and the second speech sound is output with a second occurrence frequency different from the first occurrence frequency;

performing a second trial in which the first speech sound is output with the second occurrence frequency and the second speech sound is output with the first occurrence frequency;

acquiring event-related potential contained in the electroencephalogram signal, the step acquiring: an event-related potential based on a point of outputting the first speech sound being output with the first occurrence frequency as a starting point; an event-related potential based on a point of outputting the first speech sound being output with the second occurrence frequency as a starting point; an event-related potential based on a point of outputting the second speech sound being output with the first occurrence frequency as a starting point; and an event-related potential based on a point of outputting the second speech sound being output with the second occurrence frequency as a starting point;

with respect to each of the first speech sound and the second speech sound, acquiring difference information between the event-related potential acquired during its output with the first occurrence frequency and the event-related potential acquired during its output with the second occurrence frequency, and determining whether a negative component exists in the difference information in predetermined time ranges after the first speech sound and the second speech sound are output; and when a determination result by the determining step indicates that the negative component exists, determining that the user discriminates the first speech sound and the second speech sound;

wherein the first speech sound and the second speech sound are outputted with the first occurrence frequency being X (0<X<0.5) and the second occurrence frequency being (1−X).

17. A non-transitory computer readable medium storing a computer program to be executed by a computer mounted in a speech discrimination ability determination apparatus of a speech discrimination ability determination system, wherein the computer program causes the computer to execute:

receiving an electroencephalogram signal of a user measured by a biological signal measurement section;

by referring to a speech sound database storing information of a plurality of speech sounds, determining a first speech sound and a second speech sound which are different from each other;

performing a first trial in which the first speech sound is output with a first occurrence frequency and the second speech sound is output with a second occurrence frequency different from the first occurrence frequency;

performing a second trial in which the first speech sound is output with the second occurrence frequency and the second speech sound is output with the first occurrence frequency;

acquiring event-related potential contained in the electroencephalogram signal, the step acquiring: an event-related potential based on a point of outputting the first speech sound being output with the first occurrence frequency as a starting point; an event-related potential based on a point of outputting the first speech sound being output with the second occurrence frequency as a starting point; an event-related potential based on a point of outputting the second speech sound being output with the first occurrence frequency as a starting point; and an event-related potential based on a point of outputting the second speech sound being output with the second occurrence frequency as a starting point;

with respect to each of the first speech sound and the second speech sound, acquiring difference information between the event-related potential acquired during its output with the first occurrence frequency and the event-related potential acquired during its output with the second occurrence frequency, and determining whether a negative component exists in the difference information in predetermined time ranges after the first speech sound and the second speech sound are output; and when a determination result by the MMN determination section indicates that the negative component exists, determining that the user discriminates the first speech sound and the second speech sound;

wherein the first speech sound and the second speech sound are outputted with the first occurrence frequency being X ($0<X<0.5$) and the second occurrence frequency being ($1-X$).

* * * * *